United States Patent
Lange et al.

(10) Patent No.: US 7,217,777 B2
(45) Date of Patent: May 15, 2007

(54) POLYMMONIUM-POLYSILOXANE COMPOUNDS, METHODS FOR THE PRODUCTION AND USE THEREOF

(75) Inventors: Horst Lange, Bochum (DE); Roland Wagner, Bonn (DE); Anita Witossek, Langenfeld (DE); Karl-Heinz Stachulla, Leverkusen (DE); Siegfried Teuber, Krefeld (DE); Martin Kropfgans, Odenthal (DE); Karl-Heinz Sockel, Leverkusen (DE); Annette Möller, Leverkusen (DE)

(73) Assignee: GE Bayer Silicones GmbH & Co. KG, Erkrath (DE)

( * ) Notice: Subject to any disclaimer, the term of this patent is extended or adjusted under 35 U.S.C. 154(b) by 0 days.

(21) Appl. No.: 10/333,729

(22) PCT Filed: Jul. 27, 2001

(86) PCT No.: PCT/EP01/08699

§ 371 (c)(1),
(2), (4) Date: Jul. 22, 2003

(87) PCT Pub. No.: WO02/10257

PCT Pub. Date: Feb. 7, 2002

(65) Prior Publication Data

US 2004/0048996 A1    Mar. 11, 2004

(30) Foreign Application Priority Data

Jul. 27, 2000    (DE) ................. 100 36 530
Jul. 27, 2000    (DE) ................. 100 36 541
Jul. 27, 2000    (DE) ................. 100 36 542
Jul. 27, 2000    (DE) ................. 100 36 543

(51) Int. Cl.
    *C08G 77/26*    (2006.01)
(52) U.S. Cl. .............. 528/28; 528/31; 528/26; 556/445
(58) Field of Classification Search .......... 528/28, 528/31, 26; 556/445
    See application file for complete search history.

(56) References Cited

U.S. PATENT DOCUMENTS

| 4,587,321 A | 5/1986 | Sebag et al. ............ 528/27 |
| 4,833,225 A | 5/1989 | Schaefer et al. ........ 528/28 |
| 5,196,499 A * | 3/1993 | O'Lenick, Jr. ........... 528/15 |
| 6,197,876 B1 | 3/2001 | Policello et al. ........ 524/588 |
| 6,240,929 B1 | 6/2001 | Richard et al. .......... 132/202 |

FOREIGN PATENT DOCUMENTS

| DE | 198 17 776 A | 10/1999 |
| EP | 0 282 720 A | 9/1988 |
| FR | 2 535 730 A | 5/1984 |
| WO | WO 99 50338 A | 10/1999 |
| WO | WO 00 50491 A | 8/2000 |
| WO | WO 01 41720 A | 6/2001 |

* cited by examiner

*Primary Examiner*—Kuo-Liang Peng
(74) *Attorney, Agent, or Firm*—Norris McLaughlin & Marcus PA

(57) ABSTRACT

Polyammonium-Polysiloxane compounds in which siloxane and alkylene oxide substructures are joined with each other through ammonium structures, useful as wash resistant softners.

10 Claims, No Drawings

POLYMMONIUM-POLYSILOXANE COMPOUNDS, METHODS FOR THE PRODUCTION AND USE THEREOF

The invention concerns polysiloxane compounds, methods for manufacturing them and their use.

Tertiary amino groups containing polysiloxanes have been disclosed as textile softeners in EP-A-0 441 530. The additional introduction of ethylene oxide/propylene oxide units as hydrophilizing components leads to an improvement of the effect as described in U.S. Pat. Nos. 5,591,880 and US 5,650,529. There it was proposed to position alkylene oxide units and tertiary amino groups in side chains which are connected with the siloxane main chain through ester structures. The disadvantage with this concept is the complicated esterification in the presence of tertiary amino groups. An alternative to this of bringing polyalkylene oxides having α,ω-epoxy-modified siloxanes with secondary amino functions is known from U.S. Pat. No. 5,981,681 (see also U.S. Pat. No. 5,807,956).

Likewise, the reaction of α,ω-epoxy-modified siloxanes with piperazine has been described which leads to oligomer to polymer structures with tertiary amino functions in the main chain depending upon the amount of piperazine used as described in U.S. Pat. No. 4,847,154.

α,ω-diquaternary polysiloxanes are known from U.S. Pat. No. 4,891,166. The synthesis takes place by reaction of α,ω-diepoxides with tertiary amines in the presence of acids. U.S. Pat. No. 4,833,225 discloses linear polyquaternary polysiloxanes which are synthesized through the reaction of α,ω-diepoxides with di-tertiary amines in the presence of acids. Alternatively, α,ω-halogen alkyl-modified siloxanes with di-tertiary amines are converted into polymer polyquaternary compounds in accordance with U.S. Pat. No. 4,587,321.

The substances in accordance with U.S. Pat. Nos. 4,891,166, US 4,833,225 and US 4,587,321 possess a marked tendency to shrink on solid surfaces.

U.S. Pat. No. 5,196,499 describes polysiloxane compounds with terminal quaternary ammonium groups. Polysiloxane compounds with inside place, bivalent or trivalent bridging quaternary ammonium groups are nonetheless not mentioned there.

Alkylene oxide-modified quaternary polysiloxanes have been synthesized from α,ω-OH terminated polysiloxanes and trialkoxy silanes by condensation. The quaternary ammonium structure is introduced through silane whereby the quaternary nitrogen atom has been substituted by alkylene oxide units, as already described in U.S. Pat. No. 5,625,024.

Strictly comb-like alkylene oxide-modified quaternary polysiloxanes are already known from U.S. Pat. No. 5,098,979. The hydroxyl groups of comb-like substituted polyether siloxanes are converted into the corresponding chlorohydrin derivatives with epichlorohydrin. Quaternization with tertiary amines is joined to this. The disadvantage with this synthesis is the necessity of dealing with epichlorohydrin and the relatively low reactivity of the chlorohydrin grouping during quaternization.

For this reason, the hydroxyl groups of comb-like substituted polyether siloxanes have been alternatively esterified with chloroacetic acid. The subsequent quaternization can be completed facilitated by carbonyl activation as disclosed in U.S. Pat. Nos. 5,153,294 and US 5,166,297.

Linear polyammonium structures which contain siloxane, alkylene oxide and bridging ammonium units are not accessible through the described processes.

In DE-OS 3236466, the transformation of OH-terminated siloxanes with alkoxy siloxanes containing quaternary ammonium structures furnishes reactive intermediate products which should cross-link into wash-resistant surfaces on the fiber surface with suitable cross-linking agents such as trialkylsiloxanes. A basic disadvantage of this approach is that the stability of an aqueous finishing bath cannot be guaranteed over hours and unforeseen cross-linking reactions can occur in the bath already before textile finishing. An improvement of the properties of the polysiloxane compounds is also desirable.

Consequently, it is the objective of the invention to describe polyammonium-polysiloxane compounds, their manufacture and use as wash-resistant hydrophile softeners, whereby the polyammonium-polysiloxane compounds bestow a soft touch typical of silicones upon the textiles following suitable application, and this property image is not lost even after the action of detergent formulations during repeated washing processes at if need be increased temperature. It is a further an objective of the invention to describe the use of these polyammonium-polysiloxane compounds as separate softeners according to or as softeners in formulations for washing fibers and textiles based upon non-ionogenic or anionic/non-ionogenic surfactants as well as as substances for preventing or reversing textile crumpling.

It is furthermore an objective of the invention to furnish polyammonium-polysiloxane compounds for use as wash-resistant, hydrophile softeners for textiles which can resist the attack of concentrated surfactant solutions with high fat and dirt loosening capacity. Furthermore, the polyammonium-polysiloxane compounds should resist the strongly alkaline complex formers, oxidatively acting bleaching agents and complex enzyme systems contained in modern washing agents, even if the fibers are often exposed to the action through such washing agents for hours at high temperature.

A further objective of the invention consists in furnishing treatment compounds for hair which are subject to a low ability to wash out in the presence of surfactants. Correspondingly, cosmetic formulations should also be furnished through the present invention which contain the polyammonium-polysiloxane compounds.

For this reason, it is the objective of the present invention to make available polyammonium structures which contain siloxane, alkylene oxide and bridging ammonium units which do not have the disadvantages of the state of the art.

The objective is accomplished in accordance with the invention by polysiloxane compounds in which siloxane and alkylene oxide substructures are joined with each other through ammonium structures.

The invention concerns polysiloxane compounds containing:

a) At least one polyalkylene oxide structural unit with the general formula:

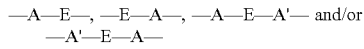

wherein
A=—CH$_2$C(O)O—, —CH$_2$CH$_2$C(O)O—, —CH$_2$CH$_2$CH$_2$C(O)O—, OC(O)CH$_2$—, —OC(O)CH$_2$CH$_2$— and/or —OC(O)CH$_2$CH$_2$CH$_2$—

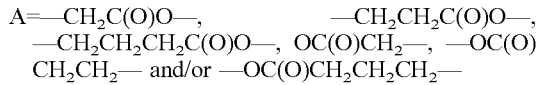

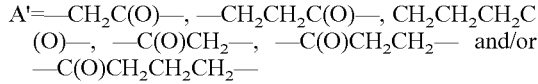

E=a polyalkylene oxide group of the general formulae:

With
q=1 to 200,
r=0 to 200,
whereby the terminal position oxygen atom of Group A binds to the terminal position —CH$_2$-group of Group E, and the terminal position carbonyl carbon atom of Group A' binds to the terminal position oxygen atom of Group E forming ester groups in each case,
and/or at least one terminal position polyalkylene oxide structural unit of the formula

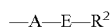

wherein A and E have the aforementioned meaning, and
$R^2$=is H, straight chain, cyclical or branched $C_1$–$C_{20}$-hydrocarbon radical, which is interrupted by —O—, or —C(O)— and substituted with —OH and can be acetylenic, olefinic or aromatic b) at least one bivalent or trivalent organic radical which contains at least one ammonium group,
c) at least one polysiloxane structural unit with the general formula:

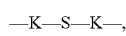

with

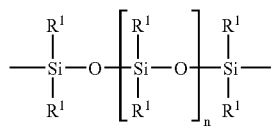

wherein $R^1$=$C_1$–$C_{22}$-alkyl, $C_1$–$C_{22}$-fluoralkyl or aryl, n=0 to 1000, and these can be identical or different if several S Groups are present in the polysiloxane compound,
K=a bivalent or trivalent straight chain, cyclical or branched $C_2$–$C_{40}$ hydrocarbon residue which is optionally interrupted by —O—, —NH—, trivalent N, —$NR^1$—, —C(O)—, —C(S)—,

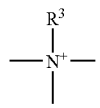

and

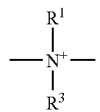

and optionally substituted with —OH, wherein
$R^1$ is defined as above, or if need be represents a bond to a bivalent radical $R^3$
$R^3$ represents a monovalent or bivalent straight chain, cyclical or branched $C_1$–$C_{20}$ hydrocarbon radical which is interrupted by —O—, —NH—, —C(O)—, —C(S)— and can be substituted with —OH, or —A—E—$R^2$, wherein A, E and $R^2$ are defined as above, whereby the residues K can be identical or different from each other, and in the event that K represents a trivalent radical, the saturation of the third valence takes place through a bonding to the above mentioned organic radical which contains at least one ammonium group,
d) at least one organic or inorganic acid radical for neutralization of the charges resulting from the ammonium group(s).

The polysiloxane compounds of the invention are characterized in that they have the components a) to d) defined above.

The polysiloxane compounds are moreover formed by binding the structural units or radicals a) to c) mentioned to one another. The component d) serves for neutralization of the positive charges resulting from the b) components.

The polysiloxane compounds of the invention can be oligomer or polymer compounds. Oligomer compounds moreover also include the case described below in which the polysiloxane compound only has one repetition unit.

Polymer polysiloxane compounds of the invention furthermore naturally arise by alternating linkage of bivalent radicals.

In the case of polymer polysiloxane compounds of the invention, the terminal position groupings result from the terminal position atom groupings of the starting materials used. This is inherently known to the specialist.

In a preferred embodiment, the polymer polysiloxane compounds of the invention are linear polyammonium-polysiloxane compounds which are composed of the structural components a) to c). The linear polymer polysiloxane compounds of the invention, especially their linear polymer main chain formed from the repetition units, can be built up alternating stringing together of polyalkylene oxide structural units a), organic radicals which contain at least one, preferably quaternary ammonium group b) and polysiloxane structural units c). That is, the free valences which are if need be present in addition in the structural components (as they can occur with trivalent radicals as components b) or with trivalent radicals K) preferably do not serve for the buildup of polymer side chains or polymer branches.

In a further embodiment, the main chain of the linear polymer polysiloxane compounds of the invention of the organic radicals which contain at least one ammonium group b) and which build up the polysiloxane structural units c) and the polyalkylene oxide structural units a) can bind to the trivalent organic ammonium group radicals as side chains. Thus, for example, the following structures result:

(Polyalkylene oxide structural unit-polysiloxane structural unit-polyalkylene oxide structural unit-preferably quaternary ammonium group radical)$_x$
(Polysiloxane structural unit-preferably quaternary ammonium group residue)$_x$-Polyalkylene oxide structural unit)$_x$
(Polysiloxane structural unit-preferably quaternary ammonium groups radical)$_x$-Polyalkylene oxide structural unit Polysiloxane compounds of the invention which have only one repetition unit according to the molar proportion of monomer starting compounds. This is inherently known to the specialist. This case leads, for example, to the polysiloxane compounds of the invention of the structure:

(terminal position polyalkylene oxide structural unit-quaternary ammonium group radical-polysiloxane structural unit-quaternary ammonium group radical-terminal position polyalkylene oxide structural unit).

The polysiloxane compounds of the invention preferably basically consist of the components a) to d), whereby the polymer polysiloxane compounds of the invention naturally have the terminal groups resulting from the transformation of the monomer starting materials. But monofunctional chain breaking agents can also be used.

With the polyalkylene oxide structural units a), it can also be a matter of bivalent radicals of the general formula:

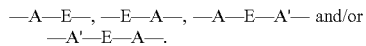
—A'—E—A—.

The radicals A or A' here mean:
A=—CH$_2$C(O)O—, —CH$_2$CH$_2$C(O)O—, —CH$_2$CH$_2$CH$_2$C(O)O—, —OC(O)CH$_2$—, OC(O)CH$_2$—, —OC(O)CH$_2$CH$_2$— and/or —OC(O)CH$_2$CH$_2$CH$_2$—
A'=—CH$_2$C(O)—, —CH$_2$CH$_2$C(O)—, CH$_2$CH$_2$CH$_2$C(O)—, —C(O)CH$_2$—, —C(O)CH$_2$—, |—C(O)CH$_2$CH$_2$— and/or —C(O)CH$_2$CH$_2$CH$_2$—

The polyalkylene oxide Group E of the general formulae: —[CH$_2$CH$_2$O]$_q$—[CH$_2$CH(CH$_3$)O]$_r$— and/or —[OCH(CH$_3$)CH$_2$]$_r$—[OCH$_2$CH$_2$]$_q$— with q=1 or 2 to 200, r=0 to 200, moreover include all possible ethylene oxide/propylene oxide groupings. Thus, it can be a matter of statistical ethylene oxide/propylene oxide copolymer groups or ethylene oxide/propylene oxide block copolymer groups with any desired arrangement of one or more ethylene oxide or propylene oxide blocks.

The binding of the radicals A or A' to Group E moreover takes place such that the terminal position oxygen atom of Group A binds to the terminal position —CH$_2$— group of Group E, and the terminal position carbonyl carbon atom of Group A' binds to the terminal position oxygen atom of Group E while forming ester groups in each case.

With the polyalkylene oxide structural units a), it can continue to be a monovalent, that is terminal position polyalkylene oxide structural unit of the formula

—A—E—R$^2$—, wherein A and E have the aforementioned meaning and R$^2$ is H, a straight chain, cyclical or branched C$_1$–C$_{20}$ hydrocarbon radical which can be interrupted by —O—, or —C(O)— and be substituted with —OH, and which can be acetylenic, olefinic or aromatic.

The component b) from which the polysiloxane compounds of the invention are composed is at least a bivalent or trivalent organic radical which contains at least one ammonium group. The bonding of the radical to the remaining components of the polysiloxane compounds of the invention preferably takes place through the nitrogen atom of one or more ammonium groups in the organic radical. The concept of "bivalent" or "trivalent" means that the organic ammonium radical has two or three free valences for forming bondings, especially to the remaining components of the polysiloxane compounds of the invention. The ammonium radical is appropriately represented by an NH$_4^+$ group in which at least two hydrogen atoms are substituted by organic groups. Preferably it is a matter of secondary or quaternary, especially preferably a quaternary ammonium group. A quaternary ammonium group is generally (see, for example, Römpp, Chemical Lexicon) defined as a group in which all four hydrogen atoms of an NH$_4^+$ group have been replaced by organic radicals.

The component c) of the polysiloxane compounds of the invention is at least one polysiloxane structural unit of the general formula:

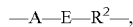
—K—S—K—,

S is therein a polysiloxane group of the general formula:

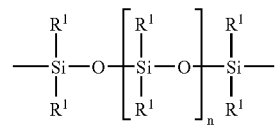

wherein R$^1$=C$_1$–C$_{22}$ alkyl, C$_1$–C$_{22}$ fluoroalkyl or aryl, preferably phenyl, n=0 to 1000, and if several Groups S are present in the polysiloxane compound, these can be identical or different.

R$^1$ is preferably C$_1$–C$_{18}$ alkyl, C$_1$–C$_{18}$ fluoroalkyl and aryl. Furthermore, R$^1$ is preferably C$_1$–C$_{18}$ alkyl, C$_1$–C$_6$ fluoroalkyl and aryl. Furthermore, R$^1$ is preferably C$_1$–C$_6$ alkyl, C$_1$–C$_6$ fluoroalkyl, more preferably C$_1$–C$_4$ fluoroalkyl, and phenyl. Even more preferably, R$^1$ is methyl, ethyl, trifluoropropyl and phenyl.

In the framework of the present invention, the term "C$_1$–C$_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl serve as examples.

In the framework of the present invention, the concept "C$_1$–C$_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are presented as examples.

In the framework of the present invention, "aryl" means unsubstituted or phenyl substituted once or several times with OH, F, Cl, CF$_3$, C$_1$–C$_6$ alkyl, C$_1$–C$_6$ alkoxy, C$_3$–C$_7$ cycloalkyl, C$_2$–C$_6$ alkenyl or phenyl. The expression can also mean naphthyl if need be.

K represents a bivalent or trivalent straight chain, cyclical or branched C$_2$–C$_{40}$ hydrocarbon radical which can be interrupted by —O—, —NH—,

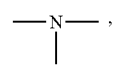

—NR$^1$—, —C(O)—, —C(S)—,

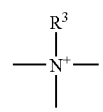

and

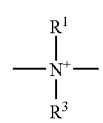

and be substituted with —OH. Here "interrupted" means that in the event of the bivalent radical, a —CH$_2$— grouping is replaced, in the case of a trivalent radical, a [paste in trivalent CH] is replaced by the aforementioned groups. This also applies for the remaining part of the description if this designation is used.

Group K bonds to the silicon atom of Group S through a carbon atom.

Group K can, as can be seen above, likewise preferably have quaternary ammonium groups so that ammonium groups result in the polysiloxane compounds of the invention in addition to the ammonium groups in the component b) mentioned.

The polysiloxane compounds of the invention can, as for example in radical K, have amino groups. The transformation of the polysiloxane groups of the invention with acids leads to their protonation. Such polysiloxane compounds having protonated amino groups are contained in the scope of the present invention.

The binding of the component c), the polysiloxane structural unit —K—S—K—, to the remaining structural components through radical K preferably does not take place through a nitrogen atom of radical K.

$R^1$ is as defined above or if need represents a bonding to a bivalent radical $R^3$ so that a cycle results.

$R^3$ represents a monovalent or bivalent straight chain, cyclical or branched $C_1$–$C_{20}$ hydrocarbon radical which is interrupted by —O—, —NH—, —C(O)—, —C(S)— and can be substituted with —OH, or —A—E—$R^2$, wherein A, E and $R^2$ are defined as above.

The residues K can be identical or different from each other, and in the event that K represents a trivalent radical, the saturation of the third valence takes place through a bonding to the above mentioned organic radical which contains at least one ammonium group.

The polysiloxane compounds of the invention furthermore contain the components d), at least one organic or inorganic acid radical for neutralization of the charges resulting from the ammonium group. Organic or inorganic acid radicals are radicals which formally result from the cleavage of one or more proteins from organic or inorganic acids and include, for example, a halogenide, such as fluorides, chlorides, bromides, sulfates, nitrates, phosphates, carboxylates, such as formiate, acetate, propionate, etc., sulfonates, sulfates, polyether carboxylates and polyether sulfates. Chloride is preferred. The organic or inorganic anionic acid radicals can be identical or different from one another as component d) of the polysiloxane compounds of the invention. Hence preferably halogenide ions result from the transformation of amines with alkyl halogenides, while, for example, carboxylates result from carboxylic acids which can be added during the conversion of bis epoxides with amines.

In a preferred embodiment of the polysiloxane compounds of the invention, K represents a bivalent or trivalent straight chain, cyclical or branched $C_2$–$C_{40}$ hydrocarbons which are interrupted by —O—, —NH—,

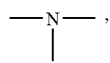

—$NR^1$—, C(O)—, —C(S)— and can be substituted with —OH, wherein $R^1$ is defined as above, and whereby the radicals K can be identical or different from each other.

The previously mentioned organic radical which contains at least one, preferably quaternary ammonium group, is preferably a radical of the general formula:

wherein $N^1$ is a quaternary ammonium group of the general formula

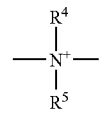

wherein $R^4$ represents a monovalent or bivalent straight chain, cyclical or branched $C_1$–$C_{20}$ hydrocarbon residue, which is interrupted by —O—, —NH—, —C(O)—, —C(S)— and can be substituted with —OH, and $R^5$ represents a monovalent straight chain, cyclical or branched $C_1$–$C_{20}$ hydrocarbon residue which can be interrupted by —O—, —NH—, —C(O)—, —C(S)— and substituted with —OH, or a single bond to a bivalent radical $R^4$ or a quadrivalent radical F, and the radicals $R^4$ and $R^5$ within the group —$N^1$F—$N^1$— as well as in the polysiloxane compound can be identical or different from one another.

F is a bivalent or quadrivalent straight chain, cyclical or branched $C_2$–$C_{30}$ hydrocarbon radical which can be interrupted by —O—, —NH—,

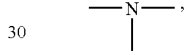

—C(O)—, —C(S)—, a siloxane chain S (whereby the above references apply for S) and substituted with —OH.

With regard to further particulars of the definitions of the quaternary ammonium group of the formula —$N^1$—F—$N^1$—(preferred embodiment etc.), refer to the explanations of the first embodiment of the present invention in which this group is realized, and which also have validity in this general context.

The previously mentioned organic radical, which contains at least one, preferably quaternary ammonium group can furthermore preferably a residue of the general formula:

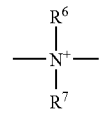

wherein $R^6$ is a monovalent or bivalent straight chain, cyclical or branched $C_1$–$C_{30}$ hydrocarbon radical, which can be interrupted by —O—, —NH—, —C(O)—, —C(S)— and be substituted with —OH, or $R^6$ can represent a single bonding to a trivalent radical K, $R^7$ is a monovalent straight chain, cyclical or branched $C_1$–$C_{20}$ hydrocarbon radical which can be interrupted by —O—, —NH—, —C(O)—, —C(S)— and be substituted with —OH. or —A—E—$R^2$; wherein —A—E—$R^2$ has the aforementioned meaning, or represents a single bond to a bivalent radical $R^6$ or to a trivalent radical K.

The radicals $R^6$ and $R^7$ can be identical or different from each other.

With regard to further particulars of the definitions of the quaternary ammonium group of the formula

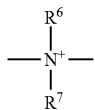

(preferred embodiments), refer to the explanations of the second, third and fourth embodiment of the present invention in which this group is realized and which also possess validity in this more general context.

The previously mentioned organic radical which contains at least one ammonium group can furthermore preferably be a radical of the general formula:

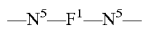

wherein $N^5$ is an ammonium group of the general formula

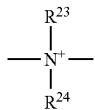

wherein
- $R^{23}$ represents hydrogen, a monovalent or bivalent straight chain, cyclical or branched $C_1$–$C_{20}$ hydrocarbon radical which can be interrupted by —O—, —NH—, —C(O)—, —C(S)— and be substituted by —OH,
- $R^{24}$ represents hydrogen, a monovalent straight chain, cyclical or branched $C_1$–$C_{20}$ hydrocarbon radical which can be interrupted by —O—, —NH—, —C(O)—, —C(S)— and be substituted with —OH, or represents a single bond to a bivalent radical $R^{23}$, and the radicals $R^{23}$ and $R^{24}$ can be identical or different from each other within the Group —$N^5$—$F^1$—$N^5$— as well as in the polysiloxane compound
- $F^1$=represents a bivalent straight chain, cyclical or branched hydrocarbon residue which can be interrupted by —O—, —NH—,

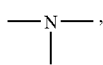

—C(O)—, —C(S)— or by a Group E, wherein E is defined as above, and wherein a majority of $N^5$ and $F^1$ can be identical or different from each other in any given case.

With regard to further particulars of definitions of the ammonium group of the formula:

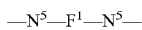

(preferred embodiments), refer to the explanations of the fifth embodiment of the present invention in which this group is realized by way of example and which also possess validity in this more general context.

The invention will be described in greater detail below on the basis of five preferred embodiments of the invention.

One particular embodiment of the invention (hereinafter referred to as the first embodiment of the invention), wherein the above-named organic group, which contains at least one, preferably quaternary, ammonium group, as component b) of the polysiloxane compounds represents a group of the general formula:

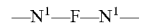

is represented by the polysiloxane compounds of the following general formula (I):

—[B—$N^1$—F—$N^1$]$_m$—  (I)

wherein
m=2 to 500,
B=—A—E—K—S—K—E—A— and, if applicable, is —A—E—A'— or —A'—E—A—,
wherein S, K, —A—E—, —E—A—, —A—E—A'— or —A'—E—A— and —$N^1$—F—$N^1$— are as defined above, and the proportion of the group —A—E—A'— or —A'—E—A— in group B can be selected such that the mass of —A—E—A'— or —A'—E—A— amounts to between 0 and 90%, preferably 0% or 0.1 to 50%, of the mass of the polysiloxane proportion S in the polymer.

The first embodiment of the invention preferably relates to linear alkylene oxide-modified polyquaternary polysiloxanes of the general formula (I'), —[B—$N^1$—F—$N^1$]$_m$—  (I')

wherein m=2 to 500
B=—A—E—K—S—K—E—A—

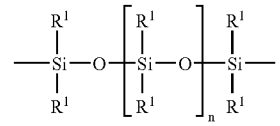

$R^1$=$C_1$–$C_{22}$-alkyl, $C_1$–$C_{22}$-fluoroalkyl or aryl,
n=0 to 1,000,
K=a divalent, straight-chain, cyclical, or branched $C_2$–$C_{20}$-hydrocarbon radical, which can be interrupted by —O—, —NH—, —$NR^1$—, —C(O)—, —C(S)— and can be substituted by —OH,
E=a polyalkylene oxide unit of the structure —[CH$_2$CH$_2$O]$_q$—[CH$_2$CH(CH$_3$)O]$_r$— in which
q is 1 to 200
r is 0 to 200 and
A is —CH$_2$C(O)O—, —CH$_2$CH$_2$C(O)O— or —CH$_2$CH$_2$CH$_2$C(O)O—,
$N^1$ is a quaternary ammonium structure

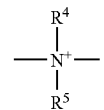

$R^4$ represents a monovalent or divalent straight chain, cyclical, or branched $C_1$–$C_{20}$-hydrocarbon radical, which can be interrupted by —O—, —NH—, —C(O)—, —C(S)—, and can be substituted by —OH, $R^5=R^4$ or represents a single bond to $R^4$ or F, F represents a divalent or tetravalent straight chain, cyclical or branched $C_2$–$C_{30}$-hydrocarbon radical, which can be interrupted by —O—, —NH—, $$-\overset{|}{\underset{|}{N}}-,$$

—C(O)—, —C(S)—, a siloxane chain S (whereby the above references apply for S) and can be substituted by —OH.

The possibility of a tetravalent substructure for F means that F can form a branched or ring system with the bordering $N^1$, hence F contributes to the quaternization of the two bordering $N^1$, via two bonds each. For an illustration of this, please refer to the piperazine structure discussed in Example 1.

In a further embodiment of the present invention, the possibility of a divalent substructure for $R^4$ means that these cases involve a structure that forms a cyclical system, wherein, in this case $R^5$ is a single covalent bond to $R^4$. Examples are morpholinyl and piperidinyl structures.

More preferred embodiments of this so-called first embodiment of the invention, along with methods for producing the above-named polysiloxane compounds of the formula (I) and/or (I'), are described below.

$R^4$ is preferably —$CH_3$, —$CH_2CH_3$, —$(CH_2)_2CH_3$, —$(CH_2)_3CH_3$, —$(CH_2)_5CH_3$, $$-CH_2CH_2\overset{H}{\underset{\|}{\underset{O}{N}}}\overset{}{C}-R^{14} \quad \text{or} \quad -CH_2CH_2\overset{H}{\underset{\|}{\underset{O}{N}}}\overset{}{C}-R^{14}$$

—$CH_2CH_2OH$, wherein $R^{14}$ is preferably a straight-chain, cyclical or branched $C_1$–$C_{18}$-hydrocarbon radical, which can be interrupted by —O—, —NH—, —C(O), —C(S)— and can be substituted by —OH.

As mentioned above, $R^4$ and $R^5$ can also together form a cyclical structure of the formulas $$\begin{array}{c} CH_2-CH_2 \\ \diagdown \quad \diagup \\ O \\ \diagup \quad \diagdown \\ CH_2-CH_2 \end{array} \quad \text{or} \quad \begin{array}{c} CH_2-CH_2 \\ \diagdown \quad \diagup \\ CH_2 \\ \diagup \quad \diagdown \\ CH_2-CH_2 \end{array}$$

For the preferred meanings for $R^1$ in the so-called first embodiment of the invention, please refer to the above explanations.

In the so-called first embodiment of the invention, $R^4$ is preferably a monovalent or divalent, straight chain, cyclical or branched $C_1$–$C_{16}$-, preferably $C3$–$C_{16}$-, hydrocarbon radical, which can be interrupted by —O—, —NH—, —C(O), —C(S)— and can be substituted by OH, preferably a $C_3$–$C_{16}$ hydrocarbon radical that can be interrupted by —O—, —NH—, —$NR^1$—, —C(O), —C(S)— and can be substituted by —OH, wherein $R^1$ has the meaning indicated above.

In the so-called first embodiment of the invention, F is preferably a divalent or tetravalent straight chain, cyclical or branched $C_2$–$C_{20}$ hydrocarbon radical that can be interrupted by —O—, —NH—, $$-\overset{|}{\underset{|}{N}}-,$$

C(O), —C(S)—, a siloxane chain S (in which the above references apply to S) and can be substituted by —OH.

In the so-called first embodiment of the invention, K is preferably —$CH_2CH_2CH_2$—, —$(CH_2)_4$—, —$(CH_2)_6$—, —$CH=CHCH_2$— and —$CH_2CH_2CH_2OCH_2CH(OH)CH_2$—.

In the so-called first embodiment of the invention, $R^{14}$ preferably represents unsubstituted $C_5$–$C_{17}$ hydrocarbon radicals that derive from the corresponding fatty acids, or hydroxylated $C_5$–$C_{17}$ groups that can be traced hydroxylated carboxylic acids, preferably saccharide carboxylic acids.

In the so-called first embodiment of the invention, $R^{14}$ further preferably represents hydroxylated groups from the group comprised of $$\begin{array}{c} | \\ CH_2 \\ | \\ CH_2 \\ | \\ CH_2OH \end{array} \quad \begin{array}{c} | \\ CH-OH \\ | \\ HO-CH \\ | \\ CH-OH \\ | \\ CH-OH \\ | \\ CH_2OH \end{array}$$

$$\begin{array}{c} CH_2OH \\ | \\ O \\ OH \\ HO \\ OH \end{array} \begin{array}{c} HO-CH \\ | \\ CH-OH \\ | \\ CH-OH \\ | \\ O-CH_2 \end{array}$$

In the so-called first embodiment of the invention, m is 2 to 100, preferably 2 to 50.

In the so-called first embodiment of the invention, n is 0 to 1,000, preferably 0 to 100, more preferably 0 to 80, and especially preferably 10 to 80.

In the so-called first embodiment of the invention, q is 1 to 200, preferably 1 to 50, more preferably 2 to 20, and especially preferably 2 to 10.

In the so-called first embodiment of the invention, r is 0 to 200, preferably 0 to 100, more preferably 0 to 50, and even more preferably 0 to 20.

The polysiloxane compounds of the so-called first embodiment as specified in the invention can be expediently produced by causing α,ω-hydrogen polysiloxanes of the general formula

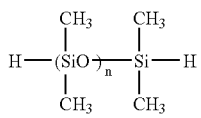

to react via hydrosilylation with 1.0 to 1.5 mol (in relation to SiH groups) of a carboxylic haloacid ester, which derives from low-molecular, oligomeric and polymeric alkenyl- or alkinyl-modified alkylene oxides of the general composition

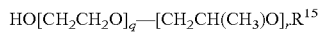

wherein q and r are defined as above, and then converting the haloacylated siloxane-alkylene oxide intermediate stages that form into polyquaternary polysiloxane derivatives using di-tertiary amines, whereby the stoichiometry of the haloacyl groups to the tertiary amino groups preferably is 1:1.

To the extent the α,ω Si—H functionalized siloxanes of the general structure

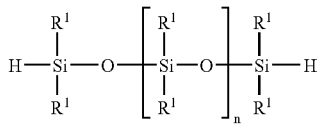

are not commercially available, these siloxanes can be produced via known methods, e.g. via equilibration (Silicone, Chemie und Technologie [Silicones, Chemistry and Technology], Vulkan Publishers, Essen 1989, pp 82–84).

The introduction of the alkylene oxide blocks occurs over the corresponding carboxylic haloacid esters of the alkylene oxides. Preferred starting materials for their synthesis are the above-named low-molecular, oligomeric and polymeric alkylene oxides of the general composition

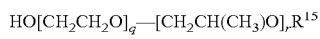

wherein the meanings for q and r are as defined above. The group $R^{15}$ expediently represents alkenyl and alkinyl structures, which are converted to K via the inherently familiar addition of ≡SiH. Examples for $R^{15}$ are allyl-butenyl-, hexenyl-, propinyl- and allylglycidyl structures. Preferred representatives with reference to the alkylene oxide block are diethylene glycol, triethylene glycol, tetraethylene glycol, the oligoethylene glycols having molar weights of 300 to 1,000 g/mol, preferably molar weights of approximately 400, 600, and 800 g/mol (400 to 800 g/mol) are used, and dipropylene glycol. The production of the alkenyl- or alkinyl-modified alkylene oxides is accomplished via the acid- or alkaline-catalyzed addition of ethylene oxide and/or propylene oxide to the corresponding alcohols, as described in U.S. Pat. No. 5,625,024, and in Organikum, Organisch-chemisches Grundpraktikum [Organic Chemistry Basic Practical Course], 17th Edition, VEB Deutscher Verlag der Wissenschaften, Berlin 1988, p 259.

The esterification of the alkenyl- or alkinyl-modified alkylene oxides takes place in a known manner (Organikum, Organisch-chemisches Grundpraktikum, 17th Edition, VEB Deutscher Verlag der Wissenschaften, Berlin 1988, pp 402–408) via reaction with the $C_2$–$C_4$ halogen carboxylic acids, their anhydrides, or acid chlorides. Chloroacetic acid and 3-chloropropionic acid are preferably used as the acid chlorides. The reaction is carried out in the absence of solvents. Details of the reaction may be taken from the examples.

In the subsequent step, the α-alkenyl/alkinyl-, ω-haloacyl-alkylene oxides are brought to react with the α,ω Si—H-functionalized siloxanes. The general implementation of hydrosilylations using unsaturated carboxylic haloacid esters is known (B. Marciniec, Comprehensive Handbook on Hydrosilylation, Pergamon Press, Oxford 1992, pp 134–137, 151–155).

In a preferred embodiment of the above-described process, first α,ω-OH-terminated reactive intermediate products are produced via hydrosilylation of the alkenyl- or alkinyl-modified alkylene oxides; in a subsequent esterification stage these intermediate products can then be converted to the corresponding α,ω-haloacyl compounds. These α,ω-haloacylated siloxane-alkylene oxide intermediate stages can be converted into polyquaternary polymers with the proper amines.

It is generally possible to use secondary amines, which, with a stoichiometric ratio of 2:1 haloacyl groups to secondary amines, supply the corresponding polyquaternary compounds. In a further preferred embodiment, the use of amines that are equipped with two tertiary amino functions is desirable, in which the stoichiometric ratio of haloacyl groups to tertiary amino groups preferably is 1:1.

These amines can be molecules with straight-chain spacers between the tertiary amino functions, such as N,N,N',N'-tetramethylethylene diamine and the corresponding higher alkene derivatives. It is also possible to use cyclical amines. N,N'-dimethylpiperazine and triethylene diamine are examples of these.

In a further embodiment of the above-described method for producing the polysiloxane compound of the first embodiment of the invention, amines having more than two tertiary amino functions are preferably used, as long as two tertiary amino functions have a sufficient reactivity advantage over the other tertiary amino functions.

N,N,N',N'',N''-pentamethyldipropylene triamine is an example of this. Molecules of this type are then viewed as difunctional.

It is further possible to position functional structures between the tertiary amino structures. Thus, it is within the scope of the invention to use α,ω-tertiary amino-modified siloxanes, which may be produced, for example, via the reaction of α,ω-SiH functionalized siloxanes with N,N-dialkylallyl amines, preferably N,N-dimethylallylamine (B. Marciniec, Comprehensive Handbook on Hydrosilylation, Pergamon Press, Oxford 1992, pp 122–124). Alternatively, for the synthesis of the α,ω-tertiary amino-modified siloxanes, corresponding α,ω-epoxy-functionalized siloxanes may be caused to react with secondary amines from the group of dialkyl amines, e.g. dimethylamine, or the cyclical amines, such as morpholine or piperidine, or secondary-tertiary diamines, such as N-methylpiperazine. Surprisingly, with this variation, it was found that in the hydrosilylation stage of allylamine derivatives, epoxide derivatives, which generally are easier to handle, such as those from the group of allylglycide ethers, can be used. In a further preferred embodiment of the above-described method, siloxanes having more than two tertiary amino groups may be used, as long as their reactivity is sufficiently differentiated, as stated above. One example of this is the aminosiloxanes, which can be synthesized in a two-stage reaction of α,ω-SiH functionalized siloxanes with allylglycide ether, and a subsequent alkylation with N-methylpiperazine.

If the secondary amines or the molecules that contain at least two tertiary amino structures are brought to react with the α,ω-haloacylated siloxane-alkylene oxide intermediate stages in the above-discussed stoichiometries, then linear products are created, in which siloxane-alkylene oxide blocks are bonded to one another via quaternary ammonium functions. With the purposeful use of amines that have more than two tertiary amino functions it is possible to synthesize regioselective products having tertiary and quaternary nitrogen atoms in their polymer structures.

In a further preferred embodiment of the above-described first embodiment of the invention, several α,ω-haloacylated siloxane-alkylene oxide intermediate stages may be used, which may differ in terms of the chain length of the siloxane components and/or the alkylene oxide components. In a further embodiment it is also possible to replace a portion of the α,ω-haloacylated siloxane-alkylene oxide intermediate stages with α,ω-haloacylated alkylene oxide derivatives without a siloxane component.

In another preferred embodiment of the above-described first embodiment of the invention, the α,ω-haloacylated siloxane-alkylene oxide intermediate stages can be bonded to various amines. The prerequisite for these advantageous forms, however, is the retention of the desired overall stoichiometry of the reaction.

Preferred anions are especially the halogenide ions, preferably chloride ions that form during quaternation. However, other anions may also be introduced via ion exchange. Anions such as carboxylates, sulfonates, sulfates, polyether carboxylates, and polyether sulfates are presented as examples.

The quaternization reactions are preferably run in polar organic solvents. Suitable solvents include, for example, alcohols from the group comprised of methanol, ethanol, i-propanol, and n-butanol; glycols from the group comprised of ethylene glycol, diethylene glycol, triethylene glycol, the methyl-, ethyl-, and butylethers of the glycols mentioned, 1,2-propylene glycol and 1,3-propylene glycol; ketones, such as acetone and methylethyl ketone, esters, such as ethyl acetate, butyl acetate, and 2-ethyl-hexyl acetate, ethers, such as tetrahydrofurane, and nitro compounds, such as nitromethane. The choice of solvent is based essentially upon the solubility of the reaction partners and the desired reaction temperature.

The reactions are run within a range of 20° C. to 130° C., preferably 4° C. to 100° C. The reaction times are based upon the temperature and the nature of the groups reacting with one another. In general, the reactions can be conducted within a span of one to 10 hours.

One particular embodiment of the invention (which hereinafter shall be referred to as the so-called second embodiment of the invention) is represented by the polysiloxane compounds of the general formula (II), $$R^2\text{—}E\text{—}A\text{—}N^2\text{—}K\text{—}S\text{—}K\text{—}N^2\text{—}A\text{—}E\text{—}R^2 \quad (II)$$

in which
S, K, —A—E—, —E—A—, and $R^2$ have the meanings given above, and
$N^2$ is an organic group containing at least one quaternary ammonium group, of the general formula

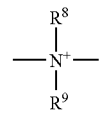

wherein
$R^8$ = a monovalent or divalent, straight-chain, cyclical or branched $C_1$–$C_{20}$-hydrocarbon radical
that can be interrupted by —O—, —NH—, —C(O), —C(S), and can be substituted by —OH,
$R^9$ represents a monovalent, straight chain, cyclical or branched $C_1$–$C_{20}$-hydrocarbon radical,
which can be interrupted by —O—, —NH—, —C(O), —C(S)—, and can be substituted by —OH, or
a single bond to a divalent group $R^8$ or to a trivalent group K, and the groups $R^8$ and $R^9$ within the polysiloxane compound of the general formula (II) can be the same as one another, or different.

The polysiloxane compounds of the second embodiment of the invention are preferably α,ω-alkylene oxide and polyquaternary-modified polysiloxanes of the general formula (II'), $$R^{16}\text{—}E\text{—}A\text{—}N^2\text{—}K\text{—}S\text{—}K\text{—}N^2\text{—}A\text{—}E\text{—}R^{16} \quad (II')$$

in which

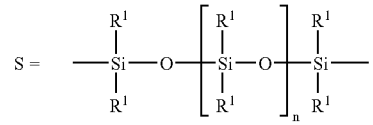

with $R^1$=$C_1$–$C_{22}$-alkyl, $C_1$–$C_{22}$-fluoroalkyl or aryl,
n=0 to 1,000,
K=a divalent or trivalent, straight-chain, cyclical or branched $C_2$–$C_{20}$ hydrocarbon radical, which can be interrupted by —O—, —NH—, $NR^1$—,

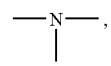

—C(O)—, —C(S)—,
and can be substituted by —OH,
$N^2$ = a quaternary ammonium structure

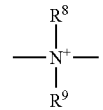

$R^8$ = a monovalent or divalent, straight-chain, cyclical or branched $C_1$–$C_{20}$ hydrocarbon
group, which can be interrupted by —O—, —NH—, —C(O)—, —C(S)—, and can be substituted by —OH,
$R^9$=$R^8$ or represents a single bond with K or $R^8$, A=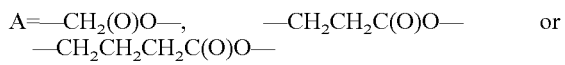

E=a polyalkylene oxide unit of the structure

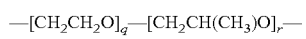

q=1 to 200 r=0 to 200 and $R^{16}$=H, straight-chain, cyclical, or branched $C_1$–$C_{20}$ hydrocarbon radical, which can be interrupted by —O— or —C(O)—, and can be substituted by —OH, and can be acetylenic, olefinic, or aromatic.

More preferred embodiments of this so-called second embodiment of the invention and methods for producing the disclosed polysiloxane compounds of the formulas (II) and (II') will be described below.

The possibility of a trivalent substructure for K means here that K can be branched, in which case it participates in the quaternization of $N^2$ with two bonds. The possibility of a divalent substructure for $R^8$ means that these cases involve a structure that forms cyclical systems, wherein $R^9$ then is a single bond at $R^2$.

$R^8$ is preferably —$CH_3$, —$CH_2CH_3$, —$(CH_2)_2CH_3$, —$(CH_2)_3CH_3$, —$(CH_2)_5CH_3$, —$CH_2CH_2OH$,

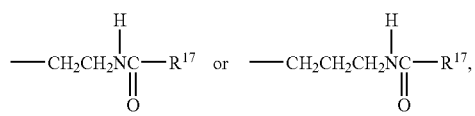

wherein $R^{17}$ is a straight-chain, cyclical or branched $C_1$–$C_{18}$ hydrocarbon radical, which can be interrupted by —O—, —NH—, —C(O)—, —C(S)—, and can be substituted by —OH.

As mentioned above, $R^8$ and $R^9$ together can also form a cyclical structure of the formulas

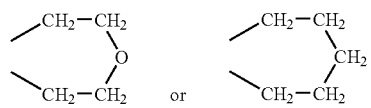

For the preferred meanings for $R^1$ in the so-called second embodiment of the invention, please refer to the preceding exposition.

In the so-called second embodiment of the invention, K is preferably a divalent or trivalent, straight-chain, cyclical or branched $C_3$–$C_{16}$ hydrocarbon radical, which can be interrupted by —O—, —NH—, —$NR^1$—,

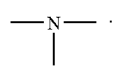

—C(O)—, —C(S)—, and can be substituted by —OH, wherein $R^1$ is defined as above.

Preferred for K, for example, are groups of the following structures:

-continued

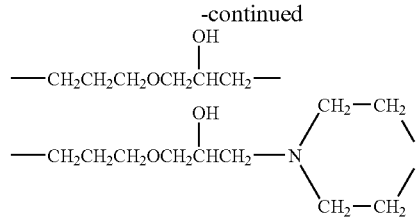

$R^8$ is preferably a monovalent or divalent, straight chain, cyclical or branched $C_1$–$C_{16}$ hydrocarbon radical, which can be interrupted by —O—, —NH—, —C(O)—, —C(S)—, and can be substituted by —OH.

$R^{16}$ is preferably a straight chain, cyclical or branched $C_1$–$C_{18}$ hydrocarbon radical that can be interrupted by —O— or —C(O)—, can be substituted by —OH, and can be acetylenic or olefinic.

Further, $R^{16}$ is preferably $C_5$–$C_{17}$-alkyl, —$CH_2CH$=$CH_2$, —$CH_2CH(OH)CH_2OCH_2CH$=$CH_2$, =$CH_2C$≡$CH$, $C(O)CH_3$, —$C(O)CH_2CH_3$.

$R^{17}$ preferably represents unsubstituted $C_5$–$C_{17}$ hydrocarbon radicals, which derive from the corresponding fatty acids, or hydroxylated $C_3$–$C_{17}$ groups, which can be traced to hydroxylated carboxylic acids, preferably to saccharide carboxylic acids.

$R^{17}$ is especially preferably chosen from the group comprised of

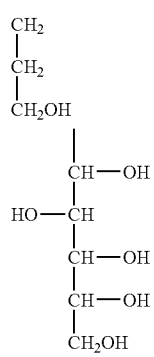

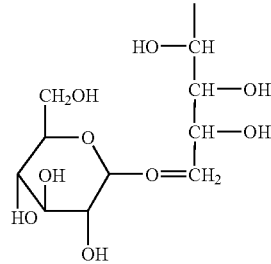

In the so-called second embodiment of the invention, n is preferably 0 to 200, more preferably 0 to 80, especially preferably 10 to 80.

In the so-called second embodiment of the invention, q is preferably 1 to 50, more preferably 2 to 20, and especially preferably 2 to 10.

In the so-called second embodiment of the invention, r is preferably 0 to 100, and more preferably 0 to 50.

In the so-called second embodiment of the invention, r is preferably 0 to 20 and more preferably 0 to 10.

The polysiloxane compounds of the so-called second embodiment of the invention can be appropriately produced in that the siloxane derivatives that contain tertiary amino groups in the α,ω position are produced via the hydrosilylation of unsaturated structures that bear tertiary amino groups with α,ω Si—H functionalized siloxanes of the general structure

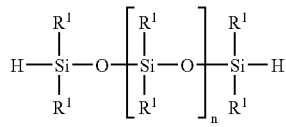

wherein $R^1$ and n have the meanings indicated above.

The starting materials for the process are α,ω Si—H functionalized siloxanes of the general structure

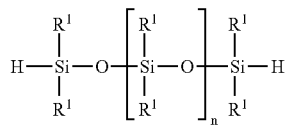

wherein $R^1$ and n have the meanings indicated above. If they are not commercially available, these siloxanes can be produced via known methods, e.g. via equilibration (Silicone, Chemie und Technologie, Vulkan-Verlag, Essen 1989, pp 82–84). The subsequent introduction of tertiary amino functions can be achieved in two ways. First, it is possible to bind unsaturated structures that bear tertiary amino functions, such as N,N-dimethylallylamine, directly to the siloxane via hydrosilylation. This process is generally known (B. Marciniec, Comprehensive Handbook on Hydrosilylation, Pergamon Press, Oxford 1992, pp 122–124).

Second, the siloxane derivatives that have tertiary amino groups in the α,ω position, and the carboxylic haloacid ester derivatives of the alkylene oxides can be caused to react in a molar ratio of siloxane to carboxylic haloacid esters of 1:2.

Preferably, the siloxane derivatives that have tertiary amino groups in the α,ω position are converted in a two-stage process via the hydrosilylation of halogenated alkenes, unsaturated carboxylic haloacid esters, and epoxy-functional alkenes, with α,ω Si—H functionalized siloxanes of the general structure

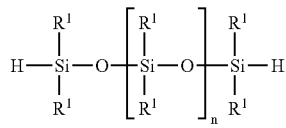

wherein $R^1$ and n have the meanings indicated above, and a subsequent alkylation of secondary compounds that bear amino functions from the group comprised of N,N-dialkylamines, cyclical secondary amines, amino amides that bear secondary amino functions, and secondary-tertiary diamines.

Preferably, allyl chloride and allyl bromide are used as the halogenated alkenes.

Those from the group comprised of chloroacetic allyl esters, chloroacetic acid propargyl esters, 3-chloropropionic acid allyl esters, and 3-chloropropionic acid propargyl esters are preferably used as the unsaturated carboxylic haloacid esters.

Vinyl cyclohexene oxide and allyl glycide ether are preferably used as epoxy functional alkenes. Dimethylamine, diethylamine, dibutylamine, diethanolamine, and N-methylglucamine are preferably used as N,N-dialkyl amines.

Morpholine and piperidine are preferably used as cyclical secondary amines.

Conversion products from diethylene triamine or dipropylene triamine with lactones, preferably γ-butyrolactone, gluconic acid-δ-lactone, and glucopyranosylarabonic acid lactone are preferably used as amino amides bearing secondary amino functions.

In other words, it is preferable to first generate reactive intermediate products via hydrosilylation, which can then be converted to tertiary amino structures in a subsequent step. Suitable starting materials for generating reactive intermediate stages include, for example, halogenated alkenes, preferably allyl chloride and allyl bromide, unsaturated carboxylic haloacid esters, preferably chloroacetic acid allyl ester, chloroacetic acid propargyl ester, 3-chloropropionic acid allyl ester, and 3-chloroproprionic acid propargyl ester, and epoxy-functional alkenes, such as vinylcyclohexene oxide and allylglycide ether. The general implementation of hydrosilylations using examples from the above-named groups of substances is also known (B. Marciniec, Comprehensive Handbook on Hydrosilylation, Pergamon Press, Oxford 1992, pp 116–121, 127–130, 134–137, 151–155).

In a subsequent step, the reactive intermediate stages can then be caused to react with compounds bearing secondary amino functions. Suitable representatives include N,N-dialkylamines, such as dimethylamine, diethylamine, dibutylamine, diethanolamine, and N-methylglucamine; cyclical secondary amines, such as morpholine and piperidine; amino amides that bear secondary amino functions, such as the conversion products of diethylene triamine or dipropylene triamine with lactones, such as γ-butyrolactone, gluconic acid-δ-lactone, and glucopyranosylarabonic acid lactone (DE-OS 4318536, Examples 11a, 12a, 13a) and secondary-tertiary diamines, such as N-methylpiperazine.

When using secondary-tertiary diamines, then epoxide derivatives should preferably be used as partners in the reaction, as in this manner alkylations of the tertiary amino function can be excluded at no additional expense.

Preferably, carboxylic haloacid esters based upon low-molecular, oligomeric and polymeric alkylene oxides of the general composition

wherein q, r, and $R^{16}$ have the meanings indicated above, and preferably monosubstituted derivatives from the group comprised of diethylene glycol, triethylene glycol, tetraethylene glycol, or oligoethylene glycols having molar weights of 300 to 1,000 g/mol, and dipropylene glycol are used.

As carboxylic haloacid esters, those from the group of oligoethylene glycols having molar weights of approximately 400, 600 and 800 g/mol (approximately 400 to 800 g/mol) are preferably used.

In other words, the introduction of the alkylene oxide blocks is preferably accomplished via the corresponding carboxylic haloacid esters of the alkylene oxides. Preferred starting materials are low-molecular, oligomeric and polymeric alkylene oxides of the general composition

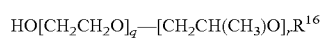

wherein q, r, and $R^{16}$ have the meanings indicated above. Preferred representatives are the correspondingly monosubstituted derivatives of diethylene glycol, triethylene glycol, tetraethylene glycol, the oligoethylene glycols having molar weights of 300 to 1,000 g/mol, preferably those from the group having molar weights of 400, 600, and 800 g/mol, as well as dipropylene glycol. The production of these ethers and esters is accomplished via known means with the acid- and alkaline-catalyzed addition of ethylene oxide and/or propylene oxide to the corresponding alcohols (Organikum, Organisch-chemisches Grundpraktikum, $17^{th}$ Edition, VEB Deutscher Verlag der Wissenschaften, Berlin 1988, p 259; U.S. Pat. No. 5,625,024) or carboxylic acids (E. Sung, W. Umbach, H. Baumann, Fette Seifen Anstrichmittel [Fats, Soaps, Paints] 73, 88 [1971]).

The subsequent synthesis of the carboxylic haloacid esters is accomplished using known methods (Organikum, Organisch-chemisches Grundpraktikum, $17^{th}$ Edition, VEB Deutscher Verlag der Wissenschaften, Berlin 1988, pp 402–408) via reaction with the $C_2$–$C_4$ halogen carboxylic acids, their anhydrides or acid chlorides. The selective synthesis of hydroxyl-functional carboxylic haloacid esters, in which $R^4$ stands for hydrogen, is accomplished via the addition of ethylene oxide and/or propylene oxide to the corresponding halogen carboxylic acids under acid conditions.

The siloxane derivatives that have tertiary amino groups in the α,ω position and the carboxylic haloacid ester derivatives of the alkylene oxides are preferably caused to react in a molar ratio of siloxane to the carboxylic haloacid ester of 1:2. With this method, products in which the siloxane and alkylene oxide blocks are bonded to one another via quaternary ammonium functions are synthesized.

With the purposeful introduction e.g. of adequately substituted piperazine rings, the synthesis regioselective products having one tertiary and one quaternary nitrogen atom in their polymeric structure can succeed. A surplus of carboxylic haloacid esters in this case leads to the start of quaternization of the remaining tertiary amino functions.

In a further preferred embodiment of the present invention, a number of siloxane components and/or alkylene oxide derivatives, each of different chain lengths, can be caused to react with one another while retaining the desired overall stoichiometry. This results in the possibility of establishing a desired siloxane chain length by using a single siloxane component, or via a selective mixture of several siloxane components. Similarly, it is also possible to present an advantageous, average alkylene oxide block length in the form of a monomodal, bimodal, or polymodal distribution.

Potential anions are the halogenide ions, preferably chloride ions that are formed during quaternization. However, other anions may also be introduced via ion exchange. Suitable examples for this include anions such as carboxylates, sulfonates, sulfates, polyether carboxylates, and polyether sulfates.

The quaternization reactions are preferably run in polar organic solvents. Suitable solvents are, e.g. alcohols, especially methanol, ethanol, i-propanol, and n-butanol; glycols, such as ethylene glycol, diethylene glycol, triethylene glycol, the methyl-, ethyl-, and butylethers of the above-named glycols, 1,2-propylene glycol, and 1,3-propylene glycol; ketones, such as acetone and methylethylketone; esters, such as ethyl acetate, butyl acetate, and 2-ethyl-hexyl acetate; ethers, such as tetrahydrofurane; and nitro compounds, such as nitromethane. The choice of solvent is based essentially upon the solubility of the reaction partners and the desired reaction temperature.

The reactions are conducted under temperatures ranging from 20° C. to 130° C., preferably 40° C. to 100° C.

One particular embodiment of the invention (which hereinafter shall be referred to as the so-called third embodiment of the invention) is represented by the polysiloxane compounds of the general formula (III):

in which S, K, and m are as defined above, $N^3$ is an organic group, which contains at least one quaternary ammonium group, of the general formula

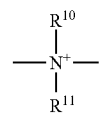

wherein $R^{10}$ represents a monovalent, straight-chain, cyclical or branched $C_1$–$C_{30}$ hydrogen group, which can be interrupted by —O—, —NH—, —C(O)—, —C(S)—, and can be substituted by —OH, or represents a single covalent bond to K, $R^{11}$=—A—E—$R^2$, wherein —A—E—$R^2$ has the meaning indicated above.

Preferably, the polysiloxane compounds of the third embodiment of the invention are alkylene oxide-modified polyquaternary polysiloxanes of the general formula (III'),

in which m is 2 to 500,

S=

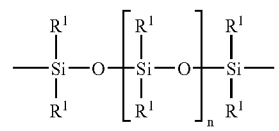

$R^1$=$C_1$–$C_{22}$ alkyl, $C_1$–$C_{22}$ fluoroalkyl or aryl,

N=0 to 1,000, $N^3$=a quaternary ammonium structure

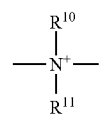

In which $R^{10}$ represents a monovalent or divalent, straight-chain, cyclical or branched $C_1$–$C_{30}$ hydrocarbon radical, which can be interrupted by —O—, —NH—, —C(O)—, —C(S)—, and can be substituted by —OH, or represents a single covalent bond to K, $R^3$ is —A—E—, with A=—$CH_2$C(O)O—, —$CH_2CH_2$C(O)O— or —$CH_2CH_2CH_2$C(O)O— and E=a polyalkylene oxide unit of the structure

q=1 to 200 r=0 to 200

$R^{18}$=H, straight-chain, cyclical or branched $C_1$–$C_{20}$ hydrocarbon radical, which can be interrupted by —O— or —C(O)—, and can be substituted by —OH, and can be acetylenic, olefinic, or aromatic, and K=a divalent or trivalent, straight-chain, cyclical or branched $C_2$–$C_{40}$ hydrocarbon radical, which can be interrupted by —O—, —NH—, —NR$^1$—,

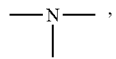

—C(O)—, —C(S)—, and can be substituted by —OH, or contains a quaternary ammonium structure $N^5$, with $N^5$=

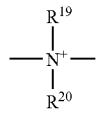

$R^{19}$ represents a monovalent or divalent, straight chain, cyclical or branched $C_1$–$C_{20}$ hydrocarbon radical,
which can be interrupted by —O—, —NH—, —C(O)—, —C(S)—, and can be substituted by —OH, or represents a single covalent bond with $R^{10}$, and $R^{20}$ is —A—E—, as defined above.

More preferred embodiments of the so-called third embodiment of the invention, along with methods for producing the above-named polysiloxane compounds of the formulae (III) and (III') will be described below.

$R^{10}$ and $R^{19}$ are, independent of one another, preferably —CH$_3$, —CH$_2$CH$_3$, —(CH$_2$)$_2$CH$_3$, —(CH$_2$)$_3$CH$_3$, —(CH$_2$)$_5$CH$_3$, —CH$_2$CH$_2$OH,

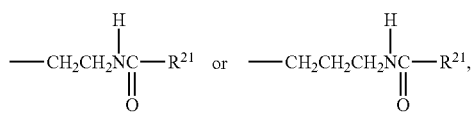

wherein $R^{21}$ is a straight-chain, cyclical or branched $C_1$–$C_{18}$ hydrocarbon radical, which can be interrupted by —O—, —NH—, —C(O)—, —C(S)—, and can be substituted by —OH.

One embodiment of the so-called third embodiment of the invention involves a divalent substructure for $R^{10}$ around a structure that forms a cyclical system, whereby $R^{10}$ then possesses a single covalent bond to K, preferably to a tertiary amino structure, or to the quaternary structure $N^5$ via $R^{19}$.

For the preferred meanings for $R^1$ in the so-called third embodiment of the invention, please refer to the above discussion.

Preferably, $R^{10}$ is a monovalent or divalent, straight chain, cyclical or branched $C_1$–$C_{25}$ hydrocarbon radical, which can be interrupted by —O—, —NH—, —C(O)—, —C(S)—, and can be substituted by —OH.

Preferably $R^{19}$ is a monovalent or divalent, straight chain, cyclical or branched $C_1$–$C_{25}$ hydrocarbon radical, which can be interrupted by —O—, —NH—, —C(O)—, —C(S)—, and can be substituted by —OH.

In the so-called third embodiment of the invention, K is still preferably a divalent or trivalent, straight-chain, cyclical or branched $C_3$–$C_{30}$ hydrocarbon radical, which can be interrupted by —O—, —NH—, —NR$^1$—,

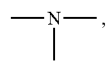

—C(O)—, —C(S)—, and can be substituted by —OH; even more preferably, K is

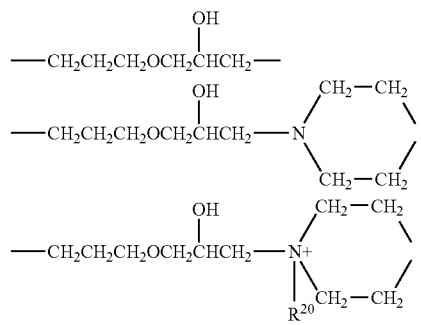

wherein $R^{20}$ is as defined above.

In the so-called third embodiment of the invention, $R^2$ or $R^{18}$ is preferably a straight chain, cyclical or branched $C_1$–$C_{18}$ hydrocarbon radical, which can be interrupted by —O— or —C(O)— and can be substituted by —OH, and can be acetylenic or olefinic. More preferably, $R^2$ or $R^{18}$ is $C^1$–$C_6$ alkyl, —CH$_2$CH=CH$_2$, —CH$_2$CH(OH) CH$_2$OCH$_2$CH=CH$_2$, —CH$_2$C≡CH, —C(O)CH$_3$ or —C(O)CH$_2$CH$_3$.

Preferably, $R^{21}$ is an unsubstituted $C_5$–$C_{17}$ hydrocarbon radical, which derives from the corresponding fatty acids or contains hydroxylated $C_3$–$C_{17}$ groups, and stems from the group of hydroxylated carboxylic acids, preferably saccharide carboxylic acids.

Thus $R^{21}$, for example, is

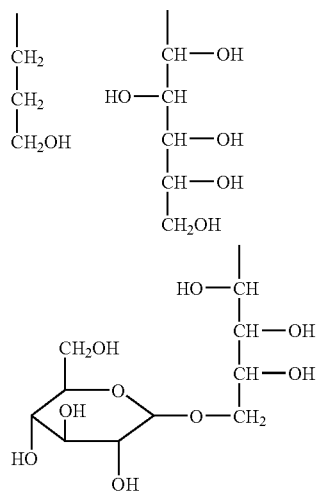

In the so-called third embodiment of the invention, m is preferably 2 to 100, and especially preferably 2 to 50, n is 0 to 100, preferably 0 to 80, and especially preferably 10 to 80, q is 1 to 50, preferably 2 to 50, and especially preferably 2 to 20, and even more preferably, q is 2 to 10, r is 0 to 100, preferably 0 to 50, especially preferably 0 to 20, and even more preferably, r is 0 to 10.

The polysiloxane compounds described in the so-called third embodiment of the invention can be appropriately produced by converting polymers that contain tertiary amino acids and are of the general structure

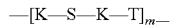

with T=

wherein K, S, $R^{10}$ and m have the meanings indicated above, with carboxylic haloacid esters transformed into quaternary ammonium compounds, which derive from alkylene oxide derivatives of the general structure $$HO[CH_2CH_2O]_q\text{—}[CH_2CH(CH_3)O]_rR^2$$

wherein q, r, and $R^2$ have the meanings indicated above, and the molar quantity of carboxylic haloacid ester is 5% of the molar quantity of tertiary amino functions.

In this, the molar quantity of carboxylic haloacid esters preferably amounts to 25%, more preferably 50%, and especially preferably 70% of the molar quantity of tertiary amino functions.

Preferably, equimolar quantities of carboxylic haloacid esters are used.

The manufacture of polymers bearing tertiary amino functions of the general structure

with T=

wherein K, S, $R^{10}$ and m have the meanings indicated above, is preferably accomplished via the alkylation of unsaturated structures that contain secondary amino functions through hydrosilylation, and are from the group comprised of N-methylallylamine or $CH_2\text{=}CHCH_2OCH_2CH(OH)CH_2NHCH_3$, with α,ω Si—H functionalized siloxanes of the general structure

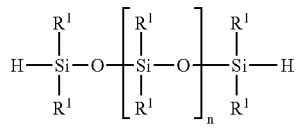

wherein $R^1$ and n have the meanings indicated above, and of extracted α,ω secondary amino-modified siloxanes that contain reactive, alkylating siloxane intermediate products, which are converted with the α,ω Si—H functionalized siloxanes of the general structure

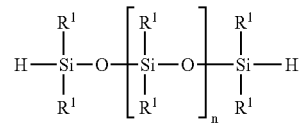

via the hydrosilylation of halogenated alkenes, unsaturated carboxylic haloacid esters, and epoxy-functional alkenes, whereby the stoichiometry of the secondary amino groups to the alkylating groups is 1:1.

More preferably, the production of the polymers of the general formula (III) or (III') that contain the tertiary amino functions, wherein K, S, $R^{10}$ and m have the meanings indicated above, takes place via the alkylation of primary amines, such as methylamine, with the reactive, alkylating siloxane intermediate products, which are produced via the hydrosilylation of halogenated alkenes, unsaturated carboxylic haloacid esters, and epoxy-functional alkenes with the α,ω Si—H functionalized siloxanes of the general structure

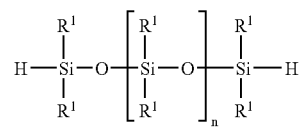

wherein the stoichiometric ratio of the primary amine to the alkylating groups is 1:2.

Preferably, allyl chloride and allyl bromide are used as the halogenated alkenes.

For the unsaturated carboxylic haloacid esters, those from the group comprised of chloroacetic allyl ester, chloroacetic acid propargyl ester, 3-chloropropionic acid allyl ester, and 3-chloropropionic acid propargyl ester are preferably used.

Vinylcyclohexene oxide and allylglycide ether are preferably used for the epoxy functional alkenes.

Further, the polymers of the general formula (III) or (III') that contain tertiary amino functions, wherein K, S, $R^{10}$ and m have the meanings indicated above, are preferably produced via the alkylation of difunctional secondary amines or corresponding secondary amino-functional amino amides with the α,ω Si—H functionalized siloxanes of the general structure

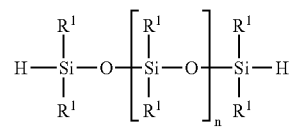

whereby the stoichiometry of the secondary amino groups to the alkylating groups is 1:1.

In the above-described embodiments for the production of the polysiloxane compounds of the so-called third embodiment of the invention, the carboxylic haloacid esters are based upon low-molecular, oligomeric and polymeric alkylene oxides of the general composition

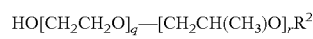

wherein q, r, and $R^2$ have the meanings indicated above, and the corresponding monosubstituted derivatives of diethylene glycol, triethylene glycol, tetraethylene glycol, the oligoethylene glycols with molar weights of 300 to 1,000 g/mol, preferably with molar weights of 400, 600, and 800 g/mol (400 to 800 g/mol), and dipropylene glycol, are used.

One particular embodiment of the invention (hereinafter referred to as the so-called fourth embodiment of the invention) is represented by the polysiloxane compounds of the general formula (IV):

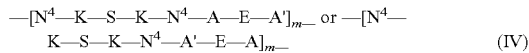  (IV)

wherein m, K, S, —A—E—A'— and —A'—E—A— are as defined above, and $N^4$ is an organic group, which contains at least one quaternary ammonium group, and is of the general formula

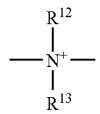

wherein $R^{12}$ is a monovalent or divalent, straight-chain, cyclical or branched $C_1$–$C_{20}$ hydrogen group, which can be interrupted by —O—, —NH—, —C(O)—, —C(S)—, and can be substituted by —OH, $R^{13}$ can have the meanings for $R^{12}$, or can represent a single covalent bond to K or $R^{12}$, and the groups $R^{12}$ and $R^{13}$ can be equal or different from one another.

Preferably, the polysiloxane compounds of the fourth embodiment of the invention are alkylene oxide-modified polyquaternary polysiloxanes of the general formula (IV'), —[$N^4$—K—S—K—$N^4$—A—E—A]$_m$—  (IV')

wherein m=2 to 500,

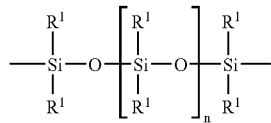

wherein $R^1$=$C_1$–$C_{22}$ alkyl, $C_1$–$C_{22}$ fluoroalkyl or aryl,
n=0 to 1,000,
K represents a divalent or trivalent, straight-chain, cyclical or branched $C_2$–$C_{20}$ hydrocarbon radical, which can be interrupted by —O—, —NH—, —$NR^1$—,

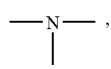

—C(O)—, —C(S)—, and can be substituted by —OH,
N is a quaternary ammonium structure

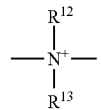

wherein $R^{12}$ is a monovalent or divalent, straight-chain, cyclical or branched $C_1$–$C_{20}$ hydrocarbon radical, which can be interrupted by —O—, —NH—, —C(O)—, —C(S)—, and can be substituted by —OH, $R^{13}$=$R^{12}$ or represents a single covalent bond with K or $R^{12}$, A=—$CH_2$C(O)O—, —$CH_2CH_2$C(O)O— or —$CH_2CH_2CH_2$C(O)O—

E=a polyalkylene oxide unit of the structure

—[$CH_2CH_2$O]$_q$—[$CH_2$CH($CH_3$)O]$_r$— with q=1 to 200 and
r=0 to 200.

More preferred embodiments of this so-called fourth embodiment of the invention, along with methods for producing the above-named polysiloxane compounds of the formula (IV) and/or (IV') will be described below.

The possibility of a trivalent substructure for K means that K can be branched, and can then participate in the quaternization of $N^4$ with two bonds.

The possibility of a divalent substructure for $R^{12}$ means that these cases involve a structure that forms cyclical systems, wherein $R^{13}$ then is a single bond to $R^{12}$.

$R^{12}$ is preferably —$CH_3$, —$CH_2CH_3$, —($CH_2$)$_2CH_3$, —($CH_2$)$_3CH_3$, —($CH_2$)$_5CH_3$, —$CH_2CH_2$OH,

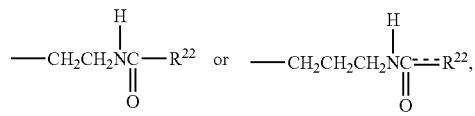

wherein $R^{22}$ is a straight-chain, cyclical or branched $C_1$–$C_{18}$ hydrocarbon radical, which can be interrupted by —O—, —NH—, —C(O)—, —C(S)—, and can be substituted by —OH.

As state above, $R^{12}$ and $R^{13}$ together can also form a cyclical structure of the formulas

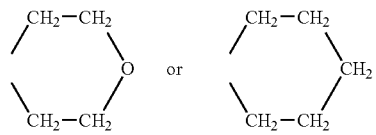

For the preferred meanings for $R^1$ in the so-called fourth embodiment of the invention, please refer to the preceding discussion.

Preferably, $R^{12}$ is a monovalent or divalent, straight chain, cyclical or branched $C_1$–$C_{16}$ hydrogen group, which can be interrupted by —O—, —NH—, —C(O)—, —C(S)—, and can be substituted by —OH. In the so-called fourth embodiment, K is preferably a divalent or trivalent, straight-chain, cyclical or branched $C_3$–$C_{16}$ hydrocarbon radical, which can be interrupted by —O—, —NH—, —$NR^1$—,

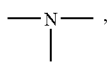

—C(O)—, —C(S)—, and can be substituted by —OH; especially preferably, K is

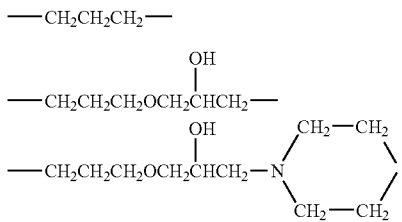

Preferably, $R^{22}$ is an unsubstituted $C_5$–$C_{17}$ hydrocarbon radical, which derives from the corresponding fatty acids or alternatively contains hydroxylated $C_3$–$C_{17}$ groups, which can be traced to hydroxylated carboxylic acids, preferably saccharide carboxylic acids.

More preferably, $R^{22}$ is:

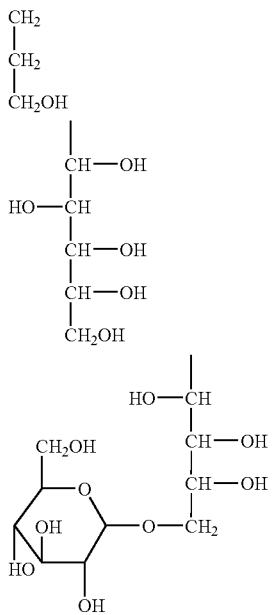

m is preferably 2 to 100, and especially preferably 2 to 50. n is 0 to 100, preferably 0 to 80, and especially preferably 10 to 80. q is 1 to 50, preferably 2 to 50, and especially preferably 2 to 20, and still more preferably, q is 2 to 10. r is 0 to 100, preferably 0 to 50, and especially preferably 0 to 20, and still more preferably, r is 0 to 10.

In the scope of the present invention, the term "$C_1$–$C_{22}$ alkyl or $C_1$–$C_{30}$ hydrocarbon radical", as used above, means aliphatic carbon-hydrogen compounds having 1 to 22 carbon atoms or 1 to 30 carbon atoms, which may be straight-chain or branched. Examples are methyl, ethyl, propyl, n-butyl, pentyl, hexyl, heptyl, nonyl, decyl, undecyl, iso-propyl, neopentyl, and 1,2,3 trimethylhexyl.

In the scope of the present invention, the term "$C_1$–$C_{22}$ fluoroalkyl", as used above, means aliphatic carbon-hydrogen compounds having 1 to 22 carbon atoms, which may be straight-chain or branched, and are substituted by at least one fluorine atom. Examples are monofluoromethyl, monofluoroethyl, 1,1,1-trifluoroethyl, perfluoroethyl, 1,1,1-trifluoropropyl, and 1,2,2-trifluorobutyl.

In the scope of the present invention, the term "aryl", as it is used above, means unsubstituted phenyl, or single or polysubstituted phenyl substituted by OH, F, CL, $CF_3$, $C_1$–$C_6$ alkyl, $C_1$–$C_6$ alkoxy, $C_3$–$C_7$ cycloalkyl, $C_2$–$C_6$ alkenyl or phenyl. The term may also mean naphthyl.

The polysiloxane compounds of the so-called fourth embodiment of the invention can be expediently produced by causing siloxane derivatives having tertiary amino groups in the α,ω position to react with alkylene oxides that contain carboxylic haloacid ester functions in the α,ω position, in an equimolar ratio of siloxane to carboxylic haloacid esters.

Preferably, the siloxane derivatives that have tertiary amino groups in the α,ω position can be produced via the hydrosilylation of unsaturated structures that contain tertiary amino groups and α,ω Si—H functionalized siloxanes of the general structure

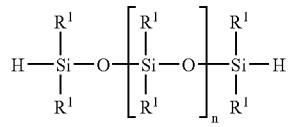

wherein $R^1$ and n have the meanings indicated above.

Furthermore, the siloxane derivatives that have tertiary amino groups in the α,ω position can be converted in a two-stage process involving the hydrosilylation of halogenated alkenes, unsaturated halogen carboxylic acid esters, and epoxy-functional alkenes, with α,ω Si—H functionalized siloxanes of the general structure

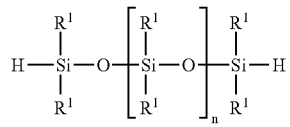

wherein $R^1$ and n have the meanings indicated above, and the subsequent alkylation of compounds that contain secondary amino functions, from the group comprised of N,N-dialkylamines, cyclical secondary amines, amino amides that contain secondary amino functions, and secondary-tertiary diamines.

Allyl chloride and allyl bromide are preferably used as the halogenated alkenes here.

As the unsaturated carboxylic haloacid esters, those from the group comprised of chloroacetic allyl ester, chloroacetic propargylester, 3-chloropropionic acid allylester, and 3-chloropropionic acid propargyl ester are preferably used.

Vinyl cyclohexene oxide and allylglycide ether are preferably used for the epoxy-functional alkenes.

Diethanolamine and N-methylglucamine are preferably used for the N,N-dialkylamines, dimethylamine, diethylamine, dibutylamine, diethanolamine, and N-methylglucamine.

Morpholine and piperidine are preferably used for the cyclical secondary amines.

Conversion products of diethylene triamine or dipropylene triamine with lactones, preferably γ-butyrolactone, gluconic acid-δ-lactone, and glucopyranosylarabonic acid lactone are preferably used for secondary amino functions containing amino amides.

For the α,ω-carboxylic haloacid esters, those that are based upon low-molecular, oligomeric and polymeric alkylene oxides of the general composition

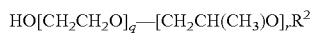

wherein q, r, and $R^2$ have the meanings disclosed in claim 1, and monosubstituted derivatives from the group comprised of diethylene glycol, triethylene glycol, tetraethylene glycol, or oligoethylene glycols having molar weights of 300 to 1,000 g/mol, and dipropylene glycol are preferably used; more preferably, those from the group of oligoethylene glycols having molar weights of approximately 400, 600 and 800 g/mol (400–800 g/mol) are used.

Thus for the syntheses of the compounds specified in the fourth embodiment of the invention, α,ω Si—H functionalized siloxanes of the general structure

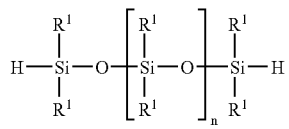

are used, wherein $R^1$ and n have the meanings indicated above. If they are not commercially available, these siloxanes can be produced via known methods, e.g. via equilibration (Silicone, Chemie und Technologie, Vulkan Verlag, Essen 1989, pp 82–84).

The subsequent introduction of tertiary amino functions can, for example, be accomplished in two ways. On the one hand, it is possible to bind unsaturated structures containing tertiary amino functions, such as N,N-dimethylallylamine, directly to the siloxane via hydrosilylation. This process is generally known in the art and is described in B. Marciniec, Comprehensive Handbook on Hydrosilylation, Pergamon Press, Oxford 1992, pp 122–124.

On the other hand, it is preferable to first generate reactive intermediate products via hydrosilylation, which can then be converted in a subsequent step into amino structures. Suitable starting materials for the generation of reactive intermediate stages include halogenated alkenes, preferably those from the group comprised of allyl chloride and allyl bromide; unsaturated carboxylic haloacid esters, preferably those from the group comprised of chloroacetic acid allylester, chloroacetic acid propargylester, 3-chloropropionic acid allylester, and 3-chloropropionic acid propargylester; and epoxy-functional alkenes, for example vinylcyclohexene oxide and allylglycide ether. The general process of hydrosilylation using representatives from the above-named groups of materials is also known in the art (B. Marciniec, Comprehensive Handbook on Hydrosilylation, Pergamon Press, Oxford 1992, pp 116–121, 127–130, 134–137, 151–155).

In a subsequent step, the reactive intermediate stages can then be caused to react with compounds that contain secondary amino functions. Suitable representatives are N,N-dialkylamines, preferably those from the group comprised of dimethylamine, diethylamine, dibutylamine, diethanolamine, and N-methylglucamine, or cyclical secondary amines, such as morpholine and piperidine; amino amides that contain secondary amino functions, for example conversion products from diethylene triamine or dipropylene triamine with lactones, such as γ-butyrolactone, gluconic acid-δ-lactone, and glycopyranosylarabonic acid lactone (as described in DE-OS 4318536, in Examples 11a, 12a, and 13a) and secondary-tertiary diamines, such as N-methylpiperazine.

When using secondary-tertiary diamines, epoxide derivatives should preferably be used as reaction partners, as in this manner alkylations of the tertiary amino functions can be excluded with no additional expenditure.

The introduction of the alkylene oxide blocks is accomplished via the corresponding α,ω-carboxylic haloacid esters of the alkylene oxides. Preferred starting materials are low-molecular, oligomeric and polymeric alkylene oxides of the general composition

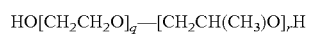

wherein q and r have the meanings indicated above. Preferred representatives are diethylene glycol, triethylene glycol, tetraethylene glycol, the oligoethylene glycols having molar weights of 300 to 1,000 g/mol, preferably having molar weights of approximately 400, 600, and 800 g/mol (400 to 800 g/mol), as well as dipropylene glycol.

The esterification is accomplished in a known-in-the-art manner (Organikum, Organisch-chemisches Grundpraktikum, $17^{th}$ Edition, VEB Deutscher Verlag der Wissenschaften, Berlin 1988, pp 402–408) via reaction with the $C_2$ to $C_4$ halogen carboxylic acids, their anhydrides, or acid chlorides.

The siloxane derivatives that have tertiary amino groups in the α,ω position and the α,ω carboxylic haloacid ester derivatives of the alkylene oxides are preferably allowed to react in equimolar quantities. In this method, products can be synthesized in which the siloxane and alkylene oxide blocks are bonded to one another via quaternary ammonium functions.

With the selective introduction, for example, of adequately substituted piperazine rings, regioselective products that have one tertiary and one quaternary nitrogen atom in their polymer structure can be synthesized.

A surplus of α,ω carboxylic haloacid esters results in cross-linkage with a corresponding increase in viscosity, resulting from an initial quaternation of the remaining tertiary amino function. A small surplus of α,ω-amino siloxane leads to a decrease in the degree of polymerization and thus a corresponding decrease in viscosity.

It is within the scope of the invention to cause several siloxane components and/or alkylene oxide derivatives of varying chain lengths to react with one another, while at the same time maintaining the desired overall stoichiometric ratio. Hence the possibility exists, e.g., of establishing a desired siloxane chain length using a single siloxane component, or by purposefully mixing several siloxane components. Similarly, it is also possible to produce an advantageous, average alkylene oxide block length in the form of a monomodal, bimodal, or polymodal dispersion.

As anions, the halogenide ions, especially chloride ions, formed during quaternization are preferably used. However, with ion exchange other anions may also be used. Possible examples of anions include those from include those from the group comprised of carboxylates, sulfonates, sulfates, polyether carboxylates and polyether sulfates.

The quaternization reactions are preferably run in polar organic solvents. Suitable solvents are those from the group comprised of alcohols, glycols, ketones, esters, ethers, and nitro compounds. The choice of solvent is based essentially upon the solubility of the reaction partners and the desired reaction temperature.

For the group of alcohols, methanol, ethanol, i-propanol and n-butanol are examples. For the group of glycols, ethylene glycol, diethylene glycol, triethylene glycol, the methyl-, ethyl-, and butylethers of the above-named glycols, 1,2-propylene glycol, and 1,3-propylene glycol are possible examples. The group of ketones includes e.g. acetone or methylethylketone. For the group of esters, ethyl acetate, butyl acetate and 2-ethyl-hexylacetate are adduced examples. The group of ethers includes tetrahydrofurane and other similar ethers. The group of nitromethanes includes those from the group of nitromethane or nitroethane.

The reactions are run within a range of 20° C. to 130° C., preferably 40° to 100° C.

One particular embodiment of the invention (hereinafter referred to as the fifth embodiment of the invention) is represented by the polysiloxane compounds of the general formula (V):

$$[-N^5-F^1-N^5-Y-]_m \qquad (V)$$

wherein

Y is a group of the formula

—K—S—K— and

wherein m, K, S, —A—E—A'— and —A'—E—A— are as defined above, the groups K, S, —A—E—A'— and —A'—E—A— within the polysiloxane compounds of the general formula (V) may be the same as or different from one another, and the molar ratio of the group —K—S—K— and the group —A—E—A'— or —A'—E—A— in the polysiloxane compound of the general formula (V) is between 100:1 and 1:100, $N^5$ is an ammonium group of the general formula

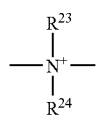

wherein $R^{23}$ represents a monovalent or divalent, straight chain, cyclical or branched $C_1$–$C_{20}$ hydrocarbon radical, which can be interrupted by —O—, —NH—, —C(O)—, —C(S), and can be substituted by —OH, $R^{24}$ represents hydrogen, a monovalent, straight chain, cyclical or branched $C_1$–$C_{20}$ hydrocarbon radical, which can be interrupted by —O—, —NH—, —C(O)—, —C(S), and can be substituted by —OH, or a single covalent bond to a divalent group $R^{23}$, and the groups $R^{23}$ and $R^{24}$ can be the same as or different from one another within the group —$N^5$—$F^1$—$N^5$— and in the polysiloxane compound, $F^1$=a divalent straight-chain, cyclical, or branched hydrocarbon radical, which can be interrupted by —O—, —NH—,

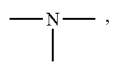

—C(O)—, —C(S), or by a group E, wherein E is as defined above, and wherein a majority of $N^5$ and $F^1$ can be the same as or different from one another.

The molar ratio of the group —K—S—K— and the group —A—E—A'— or —A'—E—A— in the polysiloxane compound of the general formula (V) lies between 100:1 and 1:100. This molar ratio can be controlled as shown below via the selection of the molar ratio of the parent compounds, especially the ratio of the α,ω-halogen carboxylic acid polyalkylene oxide ester compounds preferably used in the invention and the polysiloxane-bis epoxide compounds. The properties of the products are dependent essentially upon the ratio of the parent materials used, and upon the length of the polyalkylene oxide or polysiloxane blocks contained therein.

In a preferred embodiment of the so-called fifth embodiment of the invention, K is a divalent hydrocarbon radical having at least 4 carbon atoms, which contains one hydroxy group and can be interrupted by one oxygen atom.

In one preferred embodiment of the so-called fifth embodiment of the invention, $F^1$ represents a divalent, straight chain, cyclical or branched $C_2$–$C_{30}$ hydrocarbon radical, which can be interrupted by —O—, —NH—,

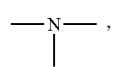

—C(O)—, —C(S), or by a group E, wherein E is as defined above, and wherein the carbon atoms that result from the group E are not counted among the 2 to 30 carbon atoms of the $C_2$–$C_{30}$ hydrocarbon radical.

In a further preferred embodiment of the so-called fifth embodiment of the invention,

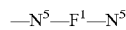

is a group of the formula:

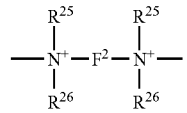

wherein $R^{25}$ is a monovalent or divalent, straight chain, cyclical or branched $C_1$–$C_{20}$ hydrocarbon radical, which can be interrupted by —O—, —NH—, —C(O)—, —C(S), and can be substituted by —OH, especially preferably methyl, $R^{26}$ represents a monovalent, straight chain, cyclical or branched $C_1$–$C_{20}$ hydrocarbon radical, which can be interrupted by —O—, —NH—, —C(O)—, —C(S), and can be substituted by —OH, especially preferably methyl, or represents a single covalent bond to a divalent group $R^{25}$, and the groups $R^{25}$ and $R^{26}$ can be the same as or different from one another within the group —$N^5$—$F^2$—$N^5$— and in the polysiloxane compound, and $F^2$=a divalent straight-chain, cyclical, or branched hydrocarbon radical, which can be interrupted by —O—, —NH—,

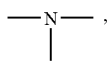

—C(O)—, —C(S).

In an even more preferred embodiment, $F^2$ is a branched, preferably straight chain $C_1$–$C_6$ alkanediyl group, wherein a 1,6-hexanediyl (or hexamethylene) group is preferred.

In a further preferred embodiment of the so-called fifth embodiment of the invention,

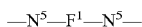

is a group of the formula:

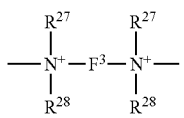

wherein
- $R^{27}$ and $R^{28}$ each are hydrogen, $C_1$–$C_6$ alkyl, or hydroxy $(C_1$–$C_6)$alkyl, preferably hydrogen, methyl, or —CH$_2$CH$_2$OH, and
- $F^3$ is a divalent, straight-chain, cyclical or branched hydrocarbon radical, which is interrupted by a group —E—, wherein E is as defined above,
- $F^3$ is especially preferably a group of the formula

—D—E—D— wherein E is as defined above and D is either a single bond or a straight chain or branched $C_1$–$C_6$ alkanediyl group, provided that D is not a single bond if it is bonded to a terminal oxygen atom of the group E.

Preferably, the group —D—E—D— is represented by a group of the formula

—D—(OCH$_2$CH$_2$)$_v$(OCH$_2$CH(CH$_3$))$_w$—O—D— wherein D is a straight chain or branched $C_1$–$C_6$ alkanediyl group and r and q are as defined above. In the group —D—(OCH$_2$CH$_2$)$_q$(OCH$_2$CH(CH$_3$))$_r$—O—D— the ethylene oxide and propylene oxide units can be positioned in any way, e.g. as statistical copolymer units or as a block copolymer unit.

- v is preferably 1 to 100, more preferably 1 to 70, even more preferably 1 to 40.
- w is preferably 0 to 100, more preferably 0 to 70, even more preferably 0 to 40.

In a further preferred embodiment of the so-called fifth embodiment of the invention, the group

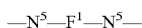

is represented by a group from the formula:

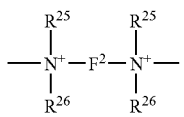

and a group from the formula:

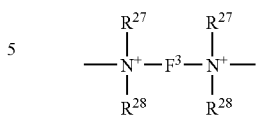

wherein the substituents have the meanings described above in each case.

This means that the polysiloxane compounds of the general formula (V) are comprised of two different types of the group —N$^5$—F$^1$—N$^5$—.

In this embodiment, the molar ratio of the group

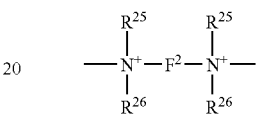

to the group

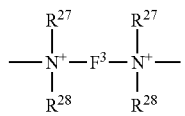

amounts appropriately to between 70:30 and 95:5, preferably between 80:20 and 90:10.

The polysiloxane compounds of the general formula (V) can be cyclical or linear. If the compounds are linear, the terminal groups result either from the bifunctional monomers or their functionalized derivatives used in production and described below, or from monoamines, which are added during the polymerization as free-radical chain terminators. The terminal groups that result from the use of the monoamine chain terminators are preferably present as ammonium groups, either via quaternization or via protonation.

In a further preferred embodiment of the so-called fifth embodiment of the invention, K [is represented] by groups of the formula

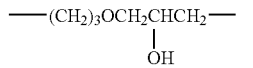
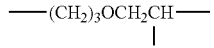
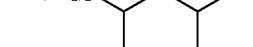
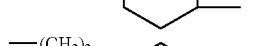
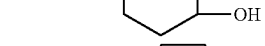
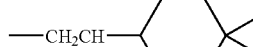
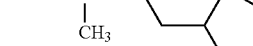

-continued

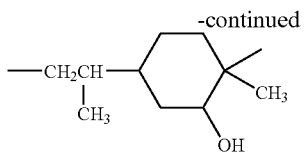

In the so-called fifth embodiment of the invention, q preferably lies within a range of 1 to 50, especially 2 to 50, especially 2 to 20, and most especially 2 to 10, and r lies within a range of 0 to 100, particularly 0 to 50, especially 0 to 20, and most especially 0 to 10.

In the so-called fifth embodiment of the invention, the organic or inorganic acid group for neutralization of the batches that result from the ammonium group(s) is expediently chosen from inorganic groups such as chloride, bromide, hydrogen sulfate, sulfate, or organic groups, such as acetate, propionate, octanoate, decanoate, dodecanoate, tetradecanoate, hexadecanoate, octadecanoate, and oleate, wherein the above-mentioned chloride and bromide preferably result from the conversion of the alkyl halogenide groups with amine groups.

Further, the polysiloxane compounds of the fifth embodiment of the invention are present in a protonated form as amine salts or as amines.

The polysiloxane compounds of the fifth embodiment of the invention are expediently produced via a method, in which first α,ω Si—H functionalized siloxanes of the general structure

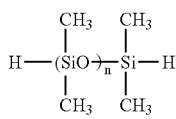

are converted, in the presence of a hydrosilylation catalyst and at temperatures of 50° to 150° C., with 1.0 to 1.5 mol, based upon SiH groups, of an alkenyl-epoxide, which has a terminal olefinic bond, wherein the alkenyl-epoxide contains at least 4 carbon atoms, and may additionally contain a non-cyclical ether group. The excess olefinic epoxide is then removed, if necessary, and the reaction product is converted with a mixture of one diamine, for example the preferred diamine of the formula

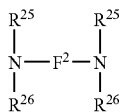

and one α,ω carboxylic haloacid ester, preferably of the formula

Z—A—E—A'—Z or Z—A—E—A'—Z wherein A—E—A' or A'—E—A are as defined above and Z is a customary nucleophilic originating group, preferably chloride or bromide, provided that Z is bonded to a terminal —CH$_2$— group,
in the presence of acid, at 40° to 120° C., wherein the molar ratio of Σ(epoxy groups+carboxylic haloacid ester groups):tertiary amino groups is appropriately approximately 1:1, and the molar ration of epoxy groups:acid is appropriately approximately 1:1.

Suitable acids that can be used in this and the process described below for producing the polysiloxane compounds include, for example, organic or inorganic acids, appropriately in aqueous solution, such as hydrohalic acids, such as hydrofluoric acid, hydrochloric acid, hydrobromic acid, sulphuric acid, nitric acid, phosphoric acid, carboxylic acids, such as formic acid, acetic acid, propanoic acid, etc., sulphonic acids, polyether carboxylic acids, etc. Preferably, $C_1$–$C_{30}$ carboxylic acids are used, especially preferably $C_{10}$–$C_{18}$ carboxylic acids. The properties of the polysiloxane compounds can be further modified based upon the selection of acids used.

Regarding the production of the α,ω Si—H functionalized siloxanes of the general structure

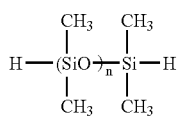

please refer to the above-described embodiments.

Parent materials for the production of the preferred α,ω carboxylic haloacid esters, preferably of the formula Z—A—E—A'—Z or Z—A—E—A'—Z wherein Z is preferably chlorine, bromine,
are expediently low-molecular, oligomeric and polymeric alkylene oxides of the general composition HO[CH$_2$CH$_2$O]$_q$—[CH$_2$CH(CH$_3$)O]$_r$H wherein q and r have the meanings indicated above. Preferred representatives are diethylene glycol, triethylene glycol, tetraethylene glycol, the oligoethylene glycols having molar weights of 300 to 1,000 g/mol, especially approximately 400, approximately 600, and approximately 800, along with dipropylene glycol.

The esterification is accomplished via known methods. For descriptions of said methods please refer to the above embodiments.

The polysiloxane compounds of the fifth embodiment of the invention are further appropriately produced via a method, wherein first α,ω Si—H functionalized siloxanes of the general structure

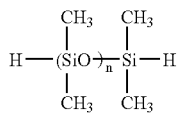

are converted, in the presence of a hydrosilylation catalyst at temperatures of 50 to 150° C., with 1.0 to 1.5 mol, based upon SiH groups, of an alkenyl epoxide, which contains a terminal olefinic bond, wherein the alkenyl epoxide contains at least 4 carbon atoms, and may also contain a non-cyclical ether group; the excess olefinic epoxide is then removed, if necessary, and the reaction product is converted, in the presence of acid, at 40° to 120° C., with a mixture of diamines, for example the preferred diamines of the formulas

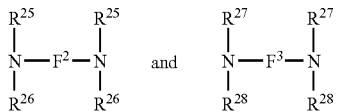

and a α,ω to carboxylic haloacid ester, preferably of the formula

Z—A—E—A'—Z or Z—A—E—A'—Z wherein A—E—A'— and A'—E—A are as defined above, and Z is a typical nucleophilic originating group, preferably chloride or bromide, provided that Z is bonded to a terminal —$CH_2$— group, converted in the presence of acid at 40 to 120° whereby the molar ratio of Σ(epoxy groups+carboxylic haloacid ester groups):Σ(primary+secondary+tertiary)amino groups is appropriately approximately 1:1, and the molar ratio of epoxy groups: acid appropriately amounts to approximately 1:1.

In the method for producing the polysiloxane compounds of the fifth embodiment of the invention, the species that contains the various amino groups, the α,ω carboxylic haloacid esters and a quantity of acid that is equimolar to the amino groups, are preferably added together to the batch.

In a further preferred embodiment of the method for producing the polysiloxane compounds of the fifth embodiment of the invention, first the epoxy derivatives, the carboxylic haloacid ester derivatives, and di-tertiary amines, preferably of the formula

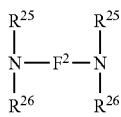

are brought to react in the presence of a quantity of acid that is equivalent to the epoxy groups, after which the alkylene oxide derivatives, which preferably contain primary or secondary amino groups, and are preferably of the formula

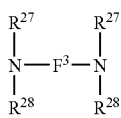

are added to the reaction mixture, if necessary with the further addition of acid to the point of equivalency.

In a further preferred embodiment of the method for producing the polysiloxane compounds of the fifth embodiment of the invention, first the carboxylic haloacid ester derivatives and di-tertiary amines, preferably those of the formula

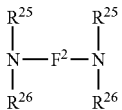

are caused to react with one another, after which the epoxy derivatives, if necessary with the addition of alkene oxide derivatives that contain primary or secondary amino groups and are preferably of the formula

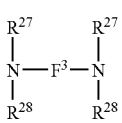

are added to the reaction mixture in the presence of a quantity of acid that is equivalent to the epoxy groups.

In a further preferred embodiment of the method for producing the polysiloxane compounds of the fifth embodiment of the invention, the alkylene oxide-modified diamines can be partially replaced by trifunctional or monofunctional alkylene oxide-modified amines, while maintaining the overall stoichiometric ratio.

In a further preferred embodiment of the method for producing the polysiloxane compounds of the fifth embodiment of the invention, the di-tertiary amines can be partially replaced by monofunctional tertiary amines, while maintaining the overall stoichiometry.

In a further preferred embodiment of the method for producing the polysiloxane compounds of the fifth embodiment of the invention, the α,ω carboxylic haloacid esters can be partially replaced by monofunctional carboxylic haloacid esters, while maintaining the overall stoichiometric ratio.

The alkylene oxide derivatives used in accordance with the fifth embodiment of the invention, which contain primary and secondary amino groups and are preferably of the formula

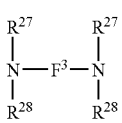

are shown, for example by the formula

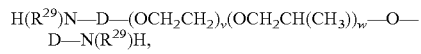

in which D, v, w, and $R^{29}$ can have the meanings of $R^{27}$ and $R^{28}$, are commercially available under the name Jeffamine® (Huntsman Corp.). Although the use of corresponding diamino derivatives is preferred, analogous trifunctional or monofunctional structures can also be partially used if a proportional cross-linking or even chain termination is intended. The portion of trifunctional, cross-linking or monofunctional, chain terminating amino derivatives amounts to a molar maximum of 10%, preferably 5%, and especially 1% of the content of the difunctional derivative.

It is also within the scope of the above-described embodiment to replace the di-tertiary amine proportionally with monofunctional tertiary amines. The portion of amines also amounts to a molar maximum of 10%, preferably 5%, and especially 1% of the content of the di-tertiary amine.

It is also within the scope of the invention to replace the α,ω carboxylic haloacid esters with monofunctional carboxylic haloacid esters. The proportion of amines also amounts to a molar maximum of 10%, preferably 5%, especially preferably 1% of the content of α,ω carboxylic haloacid esters.

With respect to the reaction, it is within the scope of the invention to add the acids, which are used in producing the polysiloxane compounds, to the batches, above the amount needed for the quaternization of the tertiary amino groups, to the point of molar equivalence with all the remaining amino groups, following the removal of the amino groups that have been alkylated by the carboxylic haloacid ester derivatives. This means that the polysiloxane compounds specified in the invention may be present as free amines or as amine salts with respect to the structure of the amino groups.

As described above, in a preferred variation of the embodiment, the species that contain the various amino groups may be added to the batch together with the carboxylic haloacid ester derivatives, if necessary with the simultaneous addition of equimolar quantities of acid. It is also within the scope of the invention, however, to cause first the epoxy derivatives, the carboxylic haloacid ester derivatives, and the di-tertiary amines to react in the presence of a quantity of acid that is equivalent to that of the epoxy groups, and then, if necessary, to add alkylene oxide derivatives that contain primary or secondary amino groups, if necessary with the addition of acids to the point of equivalence with the amino groups.

It is likewise possible to bring the carboxylic haloacid ester derivatives and the di-tertiary amines to react, forming hydrophilic blocks, and afterwards to add the epoxy derivatives, if necessary adding alkylene oxide derivatives that contain primary or secondary amino groups, in the presence of a quantity of acid that is equivalent to that of the epoxy groups to the reaction mixture.

During the time in which the individual components are being added, the sequential distribution in the polymers being formed can be influenced.

It is further within the scope of the invention to cause several siloxane components and/or alkylene oxide derivatives of various chain lengths to react, while maintaining the desired overall stoichiometry. From this, there follows, e.g., the possibility of creating a desired siloxane chain length by using a single siloxane component or by the purposeful mixture of several siloxane components. Analogously, it is possible to prepare an advantageous average alkylene oxide block length in the form of a monomodal, bimodal, or polymodal dispersion. Further, a desired share of alkylene oxides can be distributed variably between the carboxylic haloacid ester components and the amino components.

The quaternization and alkylation reactions are preferably run in polar organic solvents. Suitable solvents are, e.g., alcohols, especially methanol, ethanol, i-propanol and n-butanol; glycols, such as ethylene glycol, diethylene glycol, triethylene glycol, the methyl-, ethyl- and butyl ethers of the above-named glycols, 1,2-propylene glycol and 1,3-propylene glycol; ketones, such as acetone and methylethylketone; esters, such as ethylacetate, butylacetate and 2-ethylhexylacetate; ethers, such as tetrahydrofurane; and nitro compounds, such as nitromethane. The choice of solvents is based essentially upon the solubility of the reaction partners and the desired reaction temperature.

The reactions are preferably run within a range of 20° C. to 150° C., especially 40° C. to 100° C.

The invention further relates to the use of the above-described polysiloxane compounds in cosmetic formulations for skin and hair care, in polishing agents for treating and coating hard surfaces, in formulations for drying automobiles and other hard surfaces, for example following automatic washing, for finishing textiles and textile fibers, as separate softeners for use after textiles have been washed with non-ionogenic or anionic/non-ionogenic detergent formulations, as softeners in formulations for washing textiles that are based upon non-ionic or anionic/non-ionic surfactants, and as means for preventing or removing wrinkles in textiles.

The invention further relates to the use of the above-described polysiloxane compounds as wash-resistant, hydrophilic softeners for use in the original finishing of textiles.

The invention further relates to compositions that contain at least one of the polysiloxane compounds, together with at least one additional component that is commonly used in such a composition.

Below, a number of typical examples of these types of compositions are provided, in which the polysiloxane compounds of the invention may be advantageously used:

Typical adjuvants in these types of compositions are, e.g., those materials described in A. Domsch: Die kosmetischen Präparate [Cosmetic Preparations] Vol. I and II, $4^{th}$ Edition, Verl. fuer chem. Industrie [Publishers for the Chemical Industry], U. Ziolkowsky K G, Augsburg, and the International Cosmetic Ingredient Dictionary and Handbook $7^{th}$ Ed. 1997 by J. A. Wenninger, G. N. McEwen Vol. 1–4 by The Cosmetic, Toiletry and Fragrance Association Washington D.C.

Anionic Shampoo

This formulation example is intended as a basic formulation. Anionic shampoos customarily contain, but are not limited to, the following components:

Alkylsulfates, alkylether sulfates, sodium lauryl sulfate, sodium lauryl ether sulfate, ammonium lauryl sulfate, ammonium lauryl-ether sulfate, TEA-lauryl sulfate, TEA-lauryl-ether sulfate, alkylbenzene sulfonates, α-olefinsulfonates, paraffin sulfonates, sulfosuccinates, N-acyltaurides, sulfate-glycerides, sulfatized alkanolamides, carboxylate salts, N-acyl-amino acid salts, silicones, etc.

| Components | % |
| --- | --- |
| Ammonium lauryl sulfate | 10.00–30.00 |
| Ammonium lauryl-ether sulfate | 5.00–20.00 |
| Cocamidopropyl betaine | 0.00–15.00 |
| Lauramide DEA | 0.00–5.00 |
| Cocamide Mea | 0.00–5.00 |
| Dimethicone copolyol (dimethylsiloxane glycol copolymer) | 0.00–5.00 |
| Cyclopentasiloxane | 0.00–5.00 |
| Polysiloxane compound of the invention | 0.50–5.00 |
| Polyquaternium-10 | 0.00–2.00 |
| Preservatives | 0.00–0.50 |
| Fragrance | 0.00–5.00 |
| Deionized water | q.s. 100% |
| Sodium chloride | q.s. |

Non-Ionic Shampoo

This formulation example is intended as a basic formulation. Non-ionic shampoos customarily contain, but are not limited to, the following components:

Monoalkanolamides, monoethanolamides, monoisopropanolamides, polyhydroxy derivatives, sucrose monolaurate, polyglycerine ether, amine oxides, polyethoxylated derivatives, sorbitol derivatives, silicones, etc.

| Components | % |
|---|---|
| Lauramide DEA | 10.00–30.00 |
| Lauramide oxide | 5.00–20.00 |
| Cocamide Mea | 0.00–5.00 |
| Dimethicone copolyol | 0.00–5.00 |
| Polysiloxane compound of the invention | 0.50–5.00 |
| Preservatives | 0.00–0.50 |
| Fragrance | 0.00–5.00 |
| Deionized water | q.s. 100% |
| Sodium chloride | q.s. |

Amphoteric Shampoo

This formulation example is intended as a basic formulation. Formulations of this category customarily contain, but are not limited to, the following components:

N-alkyl-iminodipropionates, N-alkyl-iminopropionates, amino acids, amino acid derivatives, amido betaine, imidazolinium derivatives, sulfobetaines, sultaines, betaines, silicones, etc.

| Components | % |
|---|---|
| PEG-80-sorbitane laurate | 10.00–30.00 |
| Lauroamphoglycinate | 0.00–10.00 |
| Cocamidopropyl-hydroxysultain | 0.00–15.00 |
| PEG-150-distearate | 0.00–5.00 |
| Laurylether-13-carboxylate | 0.00–5.00 |
| Polysiloxane compound of the invention | 0.50–5.00 |
| Fragrance | 0.00–5.00 |
| Deionized water | q.s. 100% |
| Sodium chloride | q.s. |

Cationic Shampoo

This formulation example is intended only as a basic formulation. Formulations of this category customarily contain, but are not limited to, the following components:

Bis-quaternary ammonium compounds, bis-(trialkylammonium acetyl)diamines, amido amines, ammonium alkylesters, silicones, etc.

| Components | % |
|---|---|
| Laurylether-13-carboxylate | 10.00–30.00 |
| Isopropylmyristate | 5.00–20.00 |
| Cocamidopropyl-betaine | 0.00–15.00 |
| Lauramide DEA | 0.00–5.00 |
| Cocamide MEA | 0.00–5.00 |
| Polysiloxane compound specified in the invention | 0.50–5.00 |
| Preservatives | 0.00–0.50 |
| Fragrance | 0.00–5.00 |
| Deionized water | q.s. 100% |
| Sodium chloride | q.s. |

Solidifying Agents

This formulation example is intended only as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickeners, silicones, etc.

| Components | % |
|---|---|
| Ceteareth-20 | 0.10–10.00 |
| Steareth-20 | 0.10–10.00 |
| Stearyl alcohol | 0.10–10.00 |
| Stearamidopropyl-dimethylamine | 0.00–10.00 |
| Dicetyldimonium-chloride | 0.00–10.00 |
| Polysiloxane compound of the invention | 0.50–5.00 |
| Cyclopentasiloxane | 0.00–5.00 |
| Dimethicone | 0.00–5.00 |
| Preservatives | 0.00–0.50 |
| Fragrance | 0.00–5.00 |
| Deionized water | q.s. 100% |

"Clear Rinse-Off" Solidifying Agents

This formulation example is intended as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, etc.

| Components | % |
|---|---|
| Glycerin | 0.10–10.00 |
| Cetrimonium chloride | 0.00–10.00 |
| Polysiloxane compound of the invention | 0.50–5.00 |
| Hydroxyethyl cellulose | 0.00–5.00 |
| Preservatives | 0.00–0.50 |
| Fragrance | 0.00–5.00 |
| Deionized water | q.s. 100% |

Foam Solidifying Agents for Hair

This formulation example is intended as a basic formulation. Formulations of this category contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | % |
| --- | --- |
| Polysiloxane compound of the invention | 0.50–5.00 |
| Nonoxynol-15 | 0.00–2.00 |
| Nonoxynol-20 | 0.00–2.00 |
| Fragrance | 0.00–5.00 |
| Aerosol propellants | 0.00–20.00 |
| Preservatives | 0.00–0.50 |
| Deionized water | q.s. 100% |

Pump Spray (Solidifying Agents) for Hair

This formulation example is intended only as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, etc.

| Components | % |
| --- | --- |
| Polysiloxane compound of the invention | 0.50–5.00 |
| Cyclomethicone | 0.00–80.00 |
| Ethanol | 0.00–80.00 |
| Preservatives | 0.00–0.50 |
| Fragrance | 0.00–5.00 |
| Deionized water | q.s. 100% |

Solidifying Agent Spray for Hair

This formulation example is intended as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | % |
| --- | --- |
| Polysiloxane compound of the invention | 0.50–5.00 |
| Cyclomethicone | 0.00–80.00 |
| Ethanol | 0.00–50.00 |
| Aerosol propellants | 0.00–50.00 |
| Preservatives | 0.00–0.50 |
| Fragrance | 0.00–5.00 |
| Deionized water | q.s. 100% |

Gel Solidifying Agents for Hair

This formulation example is intended as a basic formulation. Formulations of this category customarily contain, but are not limited to, the following components: thickening agents, cellulose derivatives, acrylic acid derivatives, fixative polymers, conditioning chemicals, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, silicones, solvents, ethanol, isopropanol, isoparaffin solvents, etc.

| Components | % |
| --- | --- |
| Polysiloxane compound of the invention | 0.50–5.00 |
| Hydroxyethyl cellulose | 0.00–2.00 |
| Fragrance | 0.00–5.00 |
| Preservatives | 0.00–0.50 |
| Citric acid | 0.00–2.00 |
| Deionized water | q.s. 100% |

Styling Gel for Hair

This formulation example is intended as a basic formulation. Formulations of this category customarily contain, but are not limited to, the following components:

Fixative polymers, lacquers, acrylic acid derivatives, cellulose derivatives, vinyl derivatives, conditioning chemicals, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, etc.

| Components | % |
| --- | --- |
| Polysiloxane compound of the invention | 0.50–5.00 |
| Fixing agents | 0.10–10.00 |
| Hydroxyethyl cellulose | 0.00–2.00 |
| Fragrance | 0.00–5.00 |
| Citric acid | 0.00–2.00 |
| Deionized water | q.s. 100% |

Styling Spray for Hair

This formulation example is intended as a basic formulation. Formulations of this category customarily contain, but are not limited to, the following components:

Fixative polymers, lacquers, vinyl derivatives, fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | % |
| --- | --- |
| Polysiloxane compound of the invention | 0.50–5.00 |
| Cyclomethicone | 0.00–80.00 |

-continued

| Components | % |
|---|---|
| Fixing agents | 0.10–10.00 |
| Ethanol | 0.00–50.00 |
| Aerosol propellants | 0.00–50.00 |
| Preservatives | 0.00–0.50 |
| Fragrance | 0.00–5.00 |
| Deionized water | q.s. 100% |

Pump Spray (Styling) for Hair

This formulation example is intended as a basic formulation. Formulations of this category customarily contain, but are not limited to, the following components:

Vinyl derivatives, fixative polymers, lacquers, fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | % |
|---|---|
| Polysiloxane compound of the invention | 0.50–5.00 |
| Fixing agents | 0.10–10.00 |
| Cyclomethicone | 0.00–80.00 |
| Ethanol | 0.00–50.00 |
| Preservatives | 0.00–0.50 |
| Fragrance | 0.00–5.00 |
| Deionized water | q.s. 100% |

The use of the polysiloxane derivatives specified in the invention for applications in the hair care field produces favorable results with respect to strengthening, shine, fixing (hold), body, volume, moisture regulation, color retention, protection against environmental factors (UV, salt water, etc.), manageability, antistatic properties, ability to dye, etc.

POLYSILOXANE COMPOUND EXAMPLES

The following examples are intended to describe the present invention in greater detail, without limiting its scope.

Example 1

First Embodiment of the Invention 1a) 205.3 g (0.5 mol) of a molar-mass distributed polyether having the average structure $CH_2=CHCH_2(OCH_2CH_2)_8OH$ were placed under nitrogen at room temperature. Within 30 minutes, 63.4 g (0.55 mol) chloroacetic acid chloride were added dropwise, under intense stirring. During the dropwise addition, the temperature increased to 67° C., and an intensive formation of HCl set in. Upon completion of the dropwise addition, the batch was heated to 120° C. for 40 minutes. Finally all constituents boiling at up to 120° C. and 20 hPa were then removed via distillation. 243.6 g of a yellow, viscous liquid of the composition

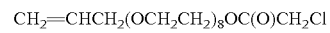

were obtained. It was determined using gas chromatography that neither chloroacetic acid chloride, chloroacetic acid, nor the OH-terminated oligoethylene glycols are present in the reaction product.

1b) 58.4 g ($6*10^{-2}$ mol) of the chloroacetic acid ester from 1a) and 0.43 g of a solution of hexachloroplatinic acid containing 2.63% platinum in 2-propanol were heated to 130° under nitrogen. Within 1.5 hours, 155.3 g ($1.2*10^{-1}$ mol) of a α,ω—SiH functionalized siloxane of the average composition

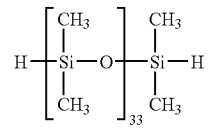

were added dropwise. After another 8 hours at 130° C., the reaction was terminated and a reaction conversion of 97% was established using SiH-determination. Over the course of the hydrosilylation reaction, a clear solution of 186 g of a yellow oil having the structure

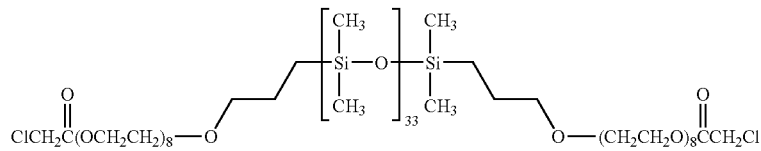

was obtained from the initially cloudy, two-phase system.

1c) 57 g ($1.6*10^{-2}$ mol) of the chloroacetic acid ester derivative from 1b) were dissolved in 100 ml 2-propanol at room temperature. 1.86 g ($1.6*10^{-2}$ mol) dimethylpiperazine was then added. The batch was heated to reflux temperature for 6 hours, after which all constituents boiling at up to 90° C. and 1.2 hPa were removed via distillation. The reaction yielded 54 g of a gray product having the structure

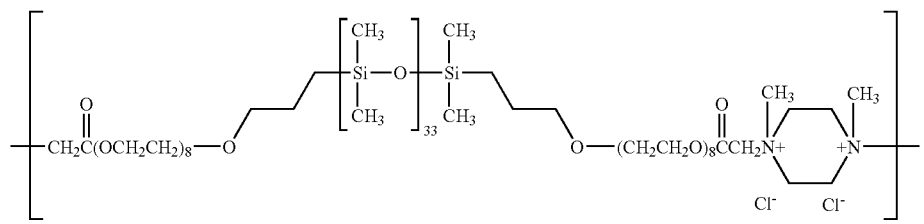

which was present first as a syrupy mass, which then crystallized over the course of 24 hours. Immediately upon termination of the reaction, and prior to the removal of the evaporable constituents, gas chromatography showed no more dimethylpiperazine.

$^{13}$C-NMR:

| Substructure | Shift (ppm) |
|---|---|
| —$\underline{C}$(O)—CH$_2$—N$^+$—CH$_2$—CH$_2$—N$^+$—CH$_2$—C(O)— | 167.3 |
| —C(O)—$\underline{C}$H$_2$—N$^+$—CH$_2$—CH$_2$—N$^+$—CH$_2$—C(O)— | 63.2/63.4 |
| —C(O)—CH$_2$—N$^+$—$\underline{C}$H$_2$—CH$_2$—N$^+$—CH$_2$—C(O)— | 60.3 |
| —C(O)—CH$_2$—N$^+$—CH$_2$—$\underline{C}$H$_2$—N$^+$—CH$_2$—C(O)— | 60.3 |
| —C(O)—CH$_2$—N$^+$—CH$_2$—CH$_2$—N$^+$—$\underline{C}$H$_2$—C(O)— | 63.2/63.4 |
| —C(O)—CH$_2$—N$^+$—CH$_2$—CH$_2$—N$^+$—CH$_2$—$\underline{C}$(O)— | 167.3 |
| —$\underline{C}$H$_3$—N$^+$≡ | 54.1 |

Example 2

First Embodiment of the Invention 2a) 181.3 g (0.5 mol) of an epoxy siloxane of the formula

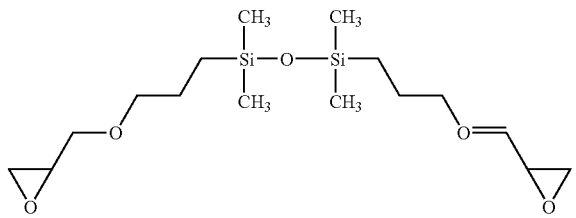

were dissolved with 101.2 g (1 mol) N-methylpiperazine in 100 ml 2-propanol, and were brought to react for 4 hours at 90° C. Following the removal of all constituents boiling at up to 130° C. and 20 hPa, 276 g of a light brown, clear amine of the formula

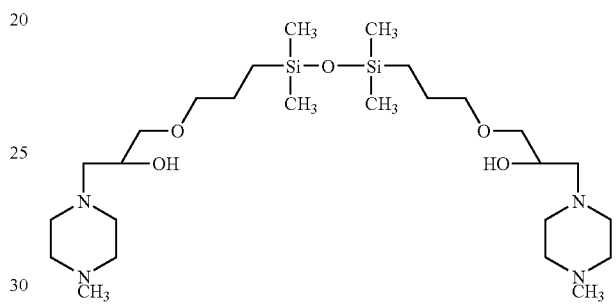

were obtained.

A reaction conversion for the two components of more than 99% was determined using gas chromatography.

2b) 57 g (1.6*10$^{-2}$ mol) of the chloroacetic acid ester derivative from 1b, and 9.01 g (1.6*10$^{-2}$ mol) of the amino siloxane from 2a were dissolved in 100 ml 2-propanol at room temperature. The reaction mixture was then heated to reflux temperature for 6 hours. All constituents boiling at up to 100° C. and 10 hPa were then removed via distillation. The reaction yielded 61.8 g of a brown product having the structure

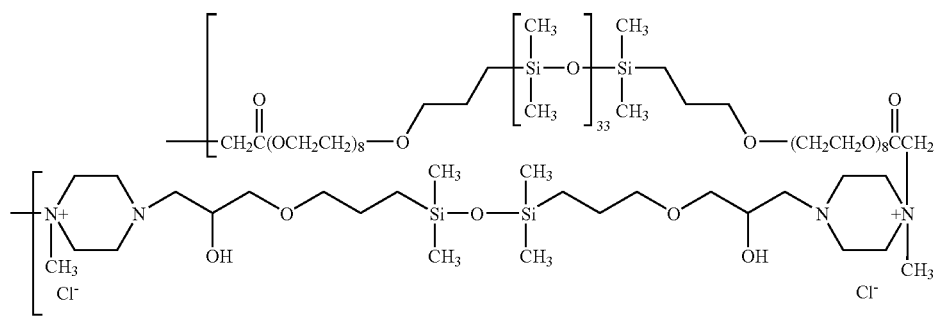

which was initially present as a syrupy mass, and solidified upon cooling without crystallizing.

| ¹³C-NMR: | |
|---|---|
| Substructure | Shift (ppm) |
| —$\underline{C}$H(OH)—CH$_2$—N—CH$_2$—CH$_2$—N$^+$—CH$_2$—C(O)— | 64.9 |
| —CH(OH)—$\underline{C}$H$_2$—N—CH$_2$—CH$_2$—N$^+$—CH$_2$—C(O)— | 53.4 |
| —CH(OH)—CH$_2$—N—$\underline{C}$H$_2$—CH$_2$—N$^+$—CH$_2$—C(O)— | 46.1 |
| —CH(OH)—CH$_2$—N—CH$_2$—$\underline{C}$H$_2$—N$^+$—CH$_2$—C(O)— | 60.2 |
| —CH(OH)—CH$_2$—N—CH$_2$—CH$_2$—N$^+$—$\underline{C}$H$_2$—C(O)— | 61.8 |
| —CH(OH)—CH$_2$—N—CH$_2$—CH$_2$—N$^+$—CH$_2$—$\underline{C}$(O)— | 166.7 |
| —$\underline{C}$H$_3$—N$^+$≡ | 50.7 |

According to the ¹³C-NMR spectrum, quaternization takes place selectively on the methyl-substituted nitrogen atoms.

Example 3

First Embodiment of the Invention

As a test for softening properties as an internal softening agent during the washing process, bleached strips of cotton, the surface of which was not finished in any other way, were subjected to a washing process in the presence of Ariel Futur®, Dash 2 in 1® containing bentonite, and the ethylene oxide-modified ester quaternary compound described in Example 1. The following boundary conditions were fulfilled.

| | Strip 1 | Strip 2 | Strip 3 |
|---|---|---|---|
| Weight of strip (g) | 11.81 | 10.81 | 10.9 |
| Quantity of water (ml) | 590 | 540 | 550 |
| Detergent | 0.59 g Ariel Futur® | 0.54 g Ariel Futur® | 0.55 g Dash 2 in 1® |
| Quaternary compound Example 1 | 0.17 g | — | — |
| Rating Ø | 1.7 | 2.4 | 1.9 |

The water was heated to 60° C., the detergents, and in the case of cotton strip 1, the compound from Example 1, were dissolved in the water. The cotton strips were washed in these solutions for 30 minutes. The strips were then rinsed five times, each time with 600 ml water, and were dried for 30 minutes at 120° C.

15 test subjects evaluated the cotton strips for softness to the touch, and assigned each a rating, with 1 indicating the softest strip and 3 indicating the roughest strip.

The results of the evaluation gave cotton strip 1 an average rating of 1.7. Cotton strip 2 was given an average rating of 2.4, and strip 3, treated with bentonite, received a rating of 1.9.

Example 4

Second Embodiment of the Invention 4a) 211.1 g (0.15 mol epoxy groups) of an epoxy siloxane of the average composition

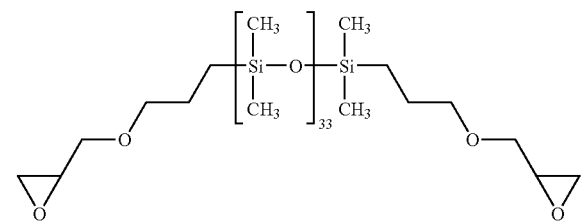

and 15.2 g (0.15 mol) N-methylpiperazine were dissolved in 225 ml i-propanol, and were heated to 90° C. for 4 hours. Following termination of the reaction, the solvent was removed via distillation in a water jet vacuum, and then in an oil pump vacuum. 217 g of a clear, yellowish product having the structure

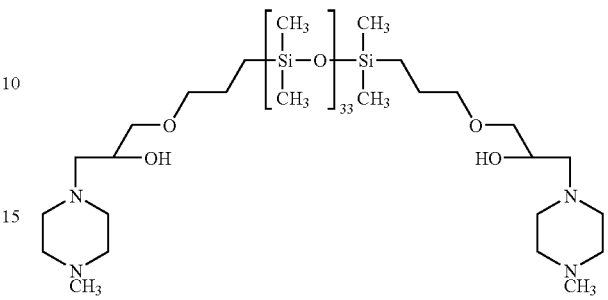

were obtained.

| ¹³C-NMR: | |
|---|---|
| Substructure | Shift (ppm) |
| —$\underline{C}$H(OH)— | 66.07 |
| —CH(OH)—$\underline{C}$H$_2$—N— | 60.74 |
| —CH(OH)—CH$_2$—N—$\underline{C}$H$_2$— | 53.20 |
| —CH(OH)—CH$_2$—N—CH$_2$—$\underline{C}$H$_2$— | 55.10 |
| —$\underline{C}$H$_3$—N═ | 45.87 |

4b) 200 g (1.21 mol) triethylene glycol monomethylether were placed under nitrogen at room temperature. Within 30 minutes, 151 g (1.34 mol) of a chloroacetic acid chloride were added dropwise, with intense stirring. During the dropwise addition, the temperature increased to 90° C., and an intense formation of HCl set in. Upon completion of the dropwise addition, the batch was heated to 130° C. for 30 minutes. All constituents boiling at up to 130° C. and 20 hPa were then removed via distillation. 301 g of a light-yellow, viscous liquid having the composition

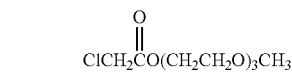

were obtained.

The purity of the ester, determined using gas chromatography, was 99%.

| ¹³C-NMR: | |
|---|---|
| Substructure | Shift (ppm) |
| —Cl$\underline{C}$H$_2$— | 40.8 |
| —ClCH$_2$—$\underline{C}$(O)— | 167.3 |
| —ClCH$_2$—CH$_2$—C(O)—O$\underline{C}$H$_2$— | 65.2 |
| —ClCH$_2$—CH$_2$—C(O)—OCH$_2$—$\underline{C}$H$_2$— | 68.7 |
| —CH$_2$—O$\underline{C}$H$_3$ | 58.8 |

4c) 19.61 g (6.5*10$^{-3}$ mol) of the α,ω-amino siloxane from Example 4a) and 3.12 g (1.3*10$^{-2}$ mol) the chloroacetic acid ester from Example 4b) were dissolved in 50 ml i-propanol under nitrogen, and then refluxed for 12 hours. Upon termination of the reaction, all constituents boiling at up to 70° C. and 20 hPa were removed. 19.7 g of a yellowish-light brown, viscous oil of the formula

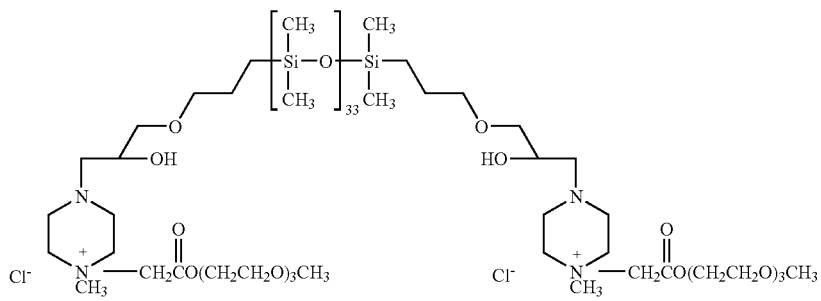

were obtained. A quantitative conversion of the ester was determined using gas chromatography.

$^{13}$C-NMR:

| Substructure | Shift (ppm) |
|---|---|
| —$\underline{C}$H(OH)— | 65.9/66.1 |
| —CH(OH)—$\underline{C}$H$_2$—N— | 52.6 |
| —CH(OH)—CH$_2$—N—$\underline{C}$H$_2$— | 45.4 |
| —CH(OH)—CH$_2$—N—$\underline{C}$H$_2$—CH$_2$— | 60.5/60.6 |
| —CH(OH)—CH$_2$—N—CH$_2$—CH$_2$—N$^+$—$\underline{C}$H$_2$— | 61.4 |
| —CH(OH)—CH$_2$—N—CH$_2$—CH$_2$—N$^+$—CH$_2$—$\underline{C}$(O)— | 169.6/169.9 |
| $\underline{C}$H$_3$—N$^+$≡ | 52.9 |
| —$\underline{C}$H$_2$—O$\underline{C}$H$_3$ | 58.6 |

According to the $^{13}$C-NMR spectrum, quaternization takes place selectively on the methyl-substituted nitrogen atoms.

Example 5

Second Embodiment of the Invention

As a test of the softening properties, bleached strips of cotton, the surface of which was not treated in any way, were subjected to a washing process in the presence of Ariel Futur®, Dash 2 in 1® containing bentonite, and the ethylene oxide-modified ester quaternary compound from Example 4. The following boundary conditions were fulfilled.

|  | Strip 1 | Strip 2 | Strip 3 |
|---|---|---|---|
| Weight of strip (g) | 13.06 | 12.92 | 13.35 |
| Quantity of water (ml) | 653 | 646 | 667 |
| Detergent | 0.65 g Ariel Futur ® | 0.64 g Dash 2 in 1 ® | 0.67 g Ariel Futur ® |
| Ester quaternary compound Example 4 | 0.2 g | — | — |
| Rating ∅ | 1.2 | 2.0 | 2.8 |

The water was heated to 60° C., the detergents, and in the case of cotton strip 1 the ester quaternary compound from Example 4, were dissolved in the water. The cotton strips were washed in these solutions for 30 minutes. The strips were then rinsed five times, each time with 600 ml water, and were dried for 30 minutes at 120° C.

14 test subjects evaluated the cotton strips for softness to the touch, and assigned each a rating, with 1 indicating the softest strip and 3 indicating the roughest strip.

The results of the evaluation gave cotton strip 1 an average rating of 1.2. The cotton strip 2 that was treated with bentonite was given an average rating of 2.0, and the strip 3, received a rating of 2.8.

Example 6

Third Embodiment of the Invention 6a) 281.6 g (0.1 mol) of an epoxy siloxane, having the average composition

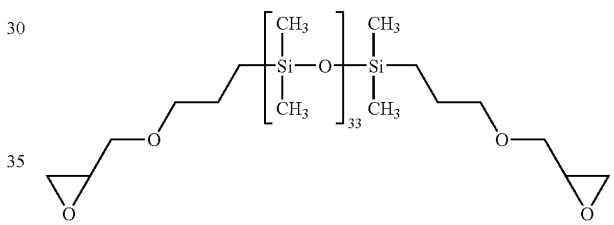

and 8.6 g (0.1 mol) piperazine were dissolved in 300 ml i-propanol, and heated to reflux temperature for 5 hours. Upon termination of the reaction, the solvent was removed via distillation, first in a water jet vacuum and then in an oil pump vacuum. 283 g of a clear, honey-like product having the structure

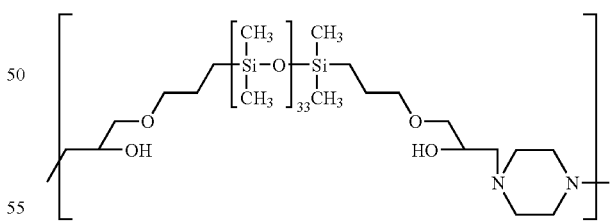

were obtained.

$^{13}$C-NMR:

| Substructure | Shift (ppm) |
|---|---|
| —$\underline{C}$H(OH)— | 66.1 |
| —CH(OH)—$\underline{C}$H$_2$—N— | 60.7 |

| <sup>13</sup>C-NMR: | |
|---|---|
| Substructure | Shift (ppm) |
| —CH(OH)—CH<sub>2</sub>—N—CH<sub>2</sub>— | 53.4 |
| —CH(OH)—CH<sub>2</sub>—N—CH<sub>2</sub>—CH<sub>2</sub>—N— | 53.4 |

6b) In a glass apparatus, 200 g (1.21 mol) triethylene glycol monomethylether were presented under nitrogen, at room temperature. Within 30 minutes, 151 g (1.34 mol) chloroacetic acid chloride were added dropwise, with intense stirring. During the dropwise addition, the temperature increased to 90° C., and intense formation of HCl set in. Upon completion of the dropwise addition, the batch was heated to 130° C. for 30 minutes. All constituents boiling at up to 130° C. and 20 hPa were then removed via distillation. The result was 301 g of a light-yellow, viscous liquid having the composition

The purity of the ester is 99%, determined using gas chromatography.

| <sup>13</sup>C-NMR: | |
|---|---|
| Substructure | Shift (ppm) |
| —ClCH<sub>2</sub>— | 40.8 |
| —ClCH<sub>2</sub>—C(O)— | 167.3 |
| —ClCH<sub>2</sub>C(O)—OCH<sub>2</sub>— | 65.2 |
| —ClCH<sub>2</sub>C(O)—OCH<sub>2</sub>CH<sub>2</sub>— | 68.7 |
| —CH<sub>2</sub>—OCH<sub>3</sub> | 58.8 |

6c) 8.71 g (6*10<sup>−3</sup> mol tertiary amino groups) of the polymeric amino siloxane from Example 6a), and 0.72 g (3*10<sup>−3</sup> mol) of the chloroacetic acid ester from Example 6b) were dissolved in 20 ml i-propanol under nitrogen, and heated to reflux temperature for 11 hours. Upon termination of the reaction, all constituents boiling at up to 70° C. and 2 hPa were removed first in a water jet vacuum and then in an oil pump vacuum. 9 g of a yellow, high-quality, viscous mass having the formula

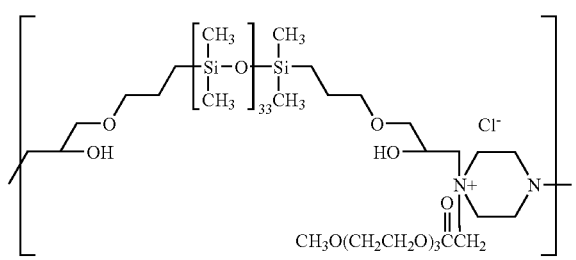

were obtained.

| <sup>13</sup>C-NMR: | |
|---|---|
| Substructure | Shift (ppm) |
| —CH(OH)— | 65.7 |
| —CH(OH)—CH<sub>2</sub>—N— | 51.7 |
| —CH(OH)—CH<sub>2</sub>—N—CH<sub>2</sub>— | 43.3 |
| —CH(OH)—CH<sub>2</sub>—N—CH<sub>2</sub>—CH<sub>2</sub>— | 64.1 |
| —CH(OH)—CH<sub>2</sub>—N—CH<sub>2</sub>—CH<sub>2</sub>—N<sup>+</sup>—CH<sub>2</sub>— | 60.7 |
| —CH(OH)—CH<sub>2</sub>—N—CH<sub>2</sub>—CH<sub>2</sub>—N<sup>+</sup>—CH<sub>2</sub>—CH(OH)— | 68.8 |
| —N<sup>+</sup>—CH<sub>2</sub>—C(O)— | 61.7 |
| —N<sup>+</sup>—CH<sub>2</sub>—C(O)— | 167.6 |

Example 7

Third Embodiment of the Invention

To test the softening properties as an internal softening agent during the washing process, bleached strips of cotton, the surface of which was not finished in any other way, were subjected to a washing process in the presence of Ariel Futur®, Dash 2 in 1® containing bentonite, and the ethylene oxide-modified polyquaternary polysiloxane ester from Example 6. The following boundary conditions were fulfilled.

| | Strip 1 | Strip 2 | Strip 3 |
|---|---|---|---|
| Weight of strip (g) | 13.36 | 13.61 | 13.44 |
| Quantity of water (ml) | 668 | 681 | 670 |
| Detergent | 0.66 g | 0.68 g | 0.65 g |
| | Ariel Futur ® | Ariel Futur ® | Dash 2 in 1 ® |
| Quaternary compound Example 6 | 0.2 g | — | — |
| Rating Ø | 1.4 | 2.7 | 1.9 |

The water was heated to 60° C., the detergents, and in the case of cotton strip 1 the ethylene oxide-modified polyquaternary polysiloxane ester from Example 6, were dissolved in the water. The cotton strips were washed in these solutions for 30 minutes. The strips were then rinsed five times, each time with 600 ml water, and were dried for 30 minutes at 120° C.

14 test subjects evaluated the cotton strips for softness to the touch, and assigned each a rating, with 1 indicating the softest strip and 3 indicating the roughest strip.

The results of the evaluation gave cotton strip 1 an average rating of 1.4. The cotton strip 2 received an average rating of 2.7, and the strip 3, which was treated with bentonite, received a rating of 1.9.

Example 8

Fourth Embodiment of the Invention 8a) 211.1 g (0.15 mol epoxy groups) of an epoxy siloxane having the average composition

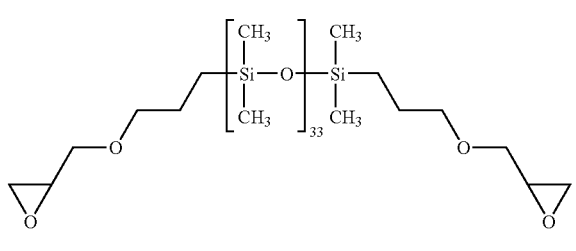

and 15.2 g (0.15 mol) N-methylpiperazine were dissolved in 225 ml i-propanol, and heated to 90° C. for 4 hours. Upon termination of the reaction, the solvent was removed via distillation first in a water jet vacuum and then in an oil pump vacuum. The result was 217 g of a clear, yellowish product having the structure

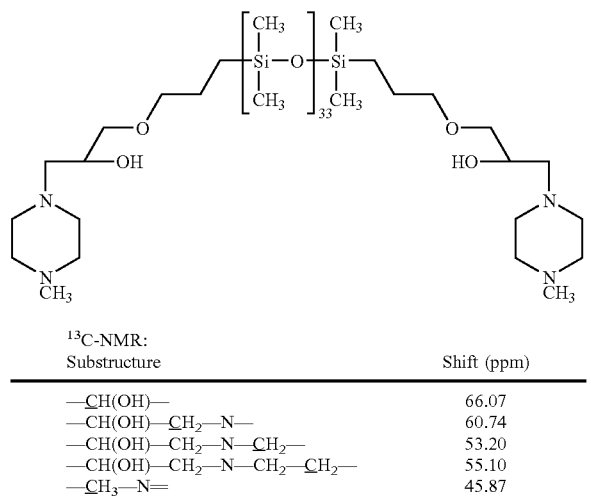

| ¹³C-NMR: Substructure | Shift (ppm) |
|---|---|
| —CH(OH)— | 66.07 |
| —CH(OH)—CH₂—N— | 60.74 |
| —CH(OH)—CH₂—N—CH₂— | 53.20 |
| —CH(OH)—CH₂—N—CH₂—CH₂— | 55.10 |
| —CH₃—N= | 45.87 |

8b) 150 g (1 mol OH groups) of a polyethylene glycol having a molecular weight of 300 g/mol (6.4 ethylene oxide units) were presented at room temperature under nitrogen. Over a span of 30 minutes, 152.4 g (1.2 mol) 3-chloropropionic acid chloride were added dropwise, under intense stirring. During the dropwise addition, the temperature rose to 70° C., and an intense formation of HCl set in. Upon completion of the dropwise addition, the batch was heated to 120° C. for 30 minutes. All constituents boiling at up to 120° C. and 20 hPa were then removed via distillation. The result was 244 g of a light-yellow, viscous liquid of the composition

It was determined using gas chromatography that the OH-terminated oligoethylene glycols are no longer present in the reaction product.

| ¹³C-NMR: Substructure | Shift (ppm) |
|---|---|
| —ClCH₂— | 39.19 |
| —ClCH₂—CH₂— | 37.49 |
| —ClCH₂—CH₂—C(O)— | 170.17 |
| —ClCH₂—CH₂—C(O)—OCH₂— | 64.01 |
| —ClCH₂—CH₂—C(O)—OCH₂—CH₂— | 68.97 |

8c) 19.61 g (6.5*10⁻³ mol) of the α,ω-amino siloxane from Example 8a) and 3.12 g (6.5*10⁻³ mol) of the α,ω-3-chloropropionic acid ester from Example 8b) were dissolved in 50 ml i-propanol under nitrogen, and heated to reflux temperature for 12 hours. Upon termination of the reaction, all constituents boiling at up to 70° C. and 20 hPa were removed. The result was 21.6 g of a yellowish wax of the formula

| ¹³C-NMR: Substructure | Shift (ppm) |
|---|---|
| —CH(OH)— | 68.9 |
| —CH(OH)—CH₂—N— | 52.8 |
| —CH(OH)—CH₂—N—CH₂— | 43.6 |
| —CH(OH)—CH₂—N—CH₂—CH₂— | 63.3 |
| —CH(OH)—CH₂—N—CH₂—CH₂—N⁺—CH₂— | 60.2 |
| —CH(OH)—CH₂—N—CH₂—CH₂—N⁺—CH₂—CH₂— | 25.5 |
| —CH(OH)—CH₂—N—CH₂—CH₂—N⁺—CH₂—CH₂—C(O)— | 165.7 |
| —CH₃—N⁺≡ | 50.6 |

According to the $^{13}$C-NMR spectrum, quaternization takes place selectively on the methyl-substituted nitrogen atoms.

Example 9

Fourth Embodiment of the Invention

9a) As with Example 8a), 181.3 g (0.5 mol) of an epoxy siloxane of the formula

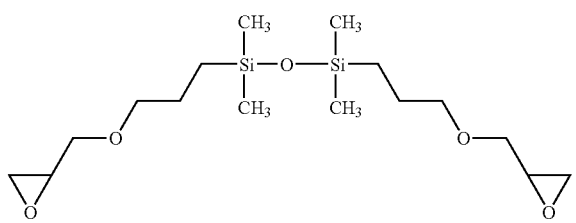

were allowed to react with 101.2 g (1 mol) N-methylpiperazine in 100 ml i-propanol. Following removal of all constituents that boil at 130° C. and 20 hPa, 276 g of a medium-brown, clear amine of the formula

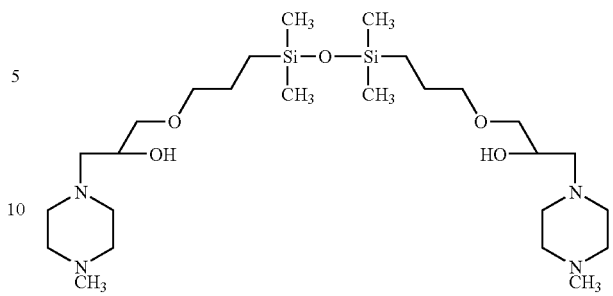

were obtained.

A reaction conversion for the two components of more than 99% was determined using gas chromatography.

9b) 6.2 g ($1.1*10^{-2}$ mol) of the amino siloxane from Example 9a), 33.21 g ($1.1*10^{-2}$ mol) of the α,ω-amino siloxane from Example 8a), and 10.59 g ($2.2*10^{-2}$ mol) of the 3-chloroproprionic ester from Example 8b) were taken up in 50 ml i-propanol, and heated to reflux temperature for 10 hours under nitrogen. Upon termination of the reaction, all constituents boiling at up to 40° C. and 20 hPa were removed. The result was 48.7 g of a brown, wax-like compound having the average composition.

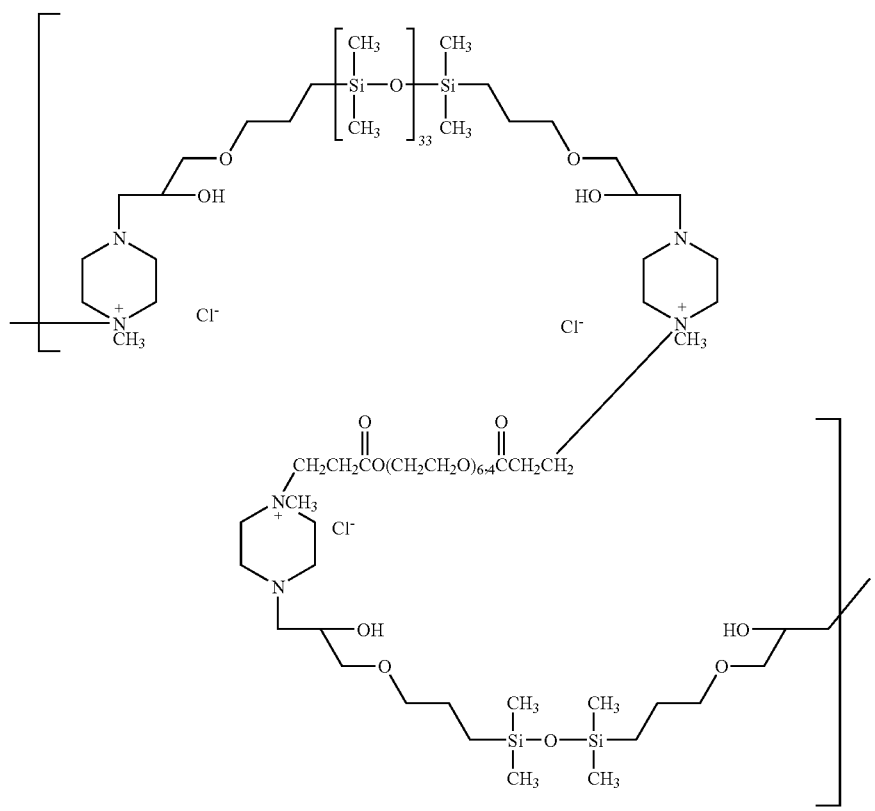

in which the two different siloxane blocks are present in a ratio of 1:1.

| | ¹³C-NMR: | |
|---|---|---|
| Substructure | | Shift (ppm) |
| —CH(OH)— | | 69.1 |
| —CH(OH)—CH₂—N— | | 52.7/ 52.9 |
| —CH(OH)—CH₂—N—CH₂— | | 43.8 |
| —CH(OH)—CH₂—N—CH₂—CH₂— | | 63.6 |
| —CH(OH)—CH₂—N—CH₂—CH₂—N⁺—CH₂— | | 60.5 |
| —CH(OH)—CH₂—N—CH₂—CH₂—N⁺—CH₂—CH₂— | | 25.5 |
| —CH(OH)—CH₂—N—CH₂—CH₂—N⁺—CH₂—CH₂—C(O)— | | 166.0 |
| —CH₃—N⁺≡ | | 50.6 |

Signals for CH₃ groups in tertiary amino structures (see NMR data from Example 8a) are no longer found.

Example 10

Fourth Embodiment of the Invention

To test the softening properties, bleached strips of cotton, the surface of which was not finished in any other way, were subjected to a washing process in the presence of Ariel Futur®, Dash 2 in 1® containing bentonite, and the ethylene oxide-modified ester quaternary compound from Example 8. The following boundary conditions were maintained.

| | Strip 1 | Strip 2 | Strip 3 |
|---|---|---|---|
| Weight of strip (g) | 13.43 | 12.94 | 13.17 |
| Quantity of water (ml) | 671 | 647 | 658 |
| Detergent | 0.67 g Ariel Futur® | 0.64 g Dash 2 in 1® | 0.65 g Ariel Futur® |
| Ester quaternary compound Example 8 | 0.2 g | — | — |
| Rating Ø | 1.6 | 1.9 | 2.5 |

The water was heated to 60° C., the detergents, and in the case of cotton strip 1, the compound from Example 1, were dissolved in the water. The cotton strips were then washed in these solutions for 30 minutes. Afterward, the strips were rinsed five times, each time with 600 ml water, and dried for 30 minutes at 120° C.

17 test subjects evaluated the cotton strips for softness to the touch, and assigned each a rating, with 1 indicating the softest strip and 3 indicating the roughest strip.

The results of the evaluation gave cotton strip 1 an average rating of 1.6. The cotton strip 2, which was treated with bentonite, was given an average rating of 1.9, and the strip 3 received an average rating of 2.5.

Example 11

Fifth Embodiment of the Invention 11a) 238 g (2.24 mol) diethylene glycol are placed at room temperature under nitrogen. Over a span of one hour, 558 g (4.93 mol) chloroacetic acid chloride are added dropwise, with intense stirring. During the dropwise addition, the temperature rises to 82° C., and an intensive formation of HCl sets in. Upon completion of the dropwise addition, the batch is heated to 130° C. for 30 minutes. All constituents boiling at up to 130° C./20 hPa are then removed via distillation. The result is 566 g of a light yellow oil having the composition ClCH₂C(O)OCH₂CH₂OCH₂CH₂OC(O)CH₂Cl The purity of the ester, determined using gas chromatography, is 99.2%.

| | ¹³C-NMR: | |
|---|---|---|
| Substructure | | Shift (ppm) |
| —ClCH₂— | | 40.7 |
| —ClCH₂—C(O)— | | 167.1 |
| —ClCH₂—C(O)—OCH₂— | | 65.2 |
| —ClCH₂—C(O)—OCH₂CH₂— | | 68.6 |

11b) In a 1-liter three-necked flask, 18 g water and 8.62 g (0.1 mol tertiary amino groups) N,N,N',N'-tetramethyl-1,6-hexanediamine are presented at room temperature. Within 5 minutes, 36.0 g (0.09 mol) dodecanoic acid in the form of a 50-% solution in 2-propanol are added. After the batch has been heated to 50° C., 194.7 g (0.09 mol epoxy groups) of an epoxy siloxane having the average composition

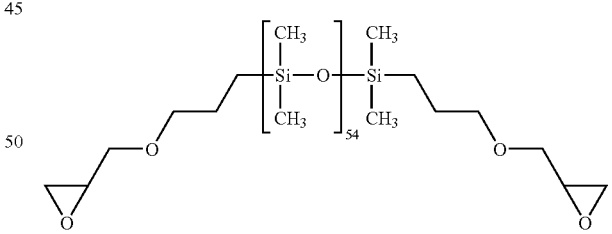

and 1.3 g (0.01 mol alkyl halogenide groups) of the ester derivative from 11a) in 22.5 ml 2-propanol are added dropwise over a period of 30 minutes. The yellow, opaque mixture is heated to reflux temperature for 6 hours. Following the removal of all constituents that are distillable in a vacuum at 100° C./2 mmHg, 210 g of a yellow, opaque material are obtained, which comprise the following structural element:

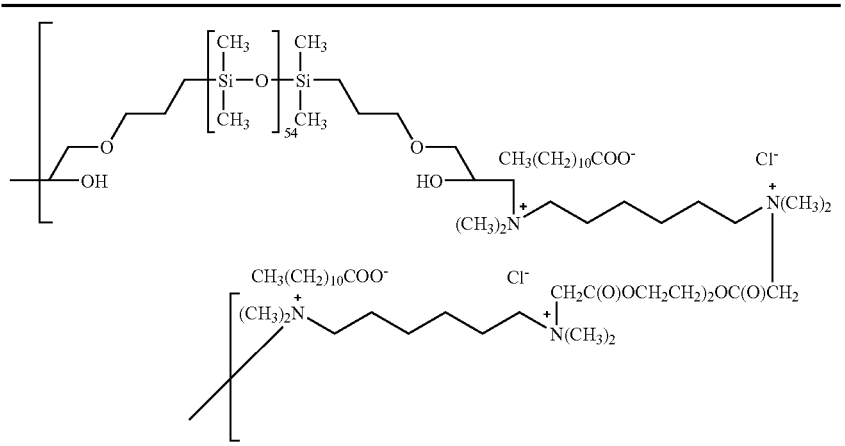

$^{13}$C-NMR:

| Substructure | Shift (ppm) |
| --- | --- |
| —CH(OH)—CH$_2$—N$^+$[(CH$_3$)$_2$]—CH$_2$—CH$_2$ | 65.3 |
| —CH(OH)—CH$_2$—N$^+$[(CH$_3$)$_2$]—CH$_2$—CH$_2$ | 64.6 |
| —CH(OH)—CH$_2$—N$^+$[(CH$_3$)$_2$]—CH$_2$—CH$_2$ | 53.1/53.3 |
| —CH(OH)—CH$_2$—N$^+$[(CH$_3$)$_2$]—CH$_2$—CH$_2$ | 64.8 |
| —CH(OH)—CH$_2$—N$^+$[(CH$_3$)$_2$]—CH$_2$—CH$_2$ | 23.4 |
| —O—C(O)—CH$_2$—N$^+$[(CH$_3$)$_2$]—CH$_2$—CH$_2$ | 174.2 |
| —O—C(O)—CH$_2$—N$^+$[(CH$_3$)$_2$]—CH$_2$—CH$_2$ | 62.0 |
| —O—C(O)—CH$_2$—N$^+$[(CH$_3$)$_2$]—CH$_2$—CH$_2$ | 53.7 |

Example 12

Fifth Embodiment of the Invention) and Comparison Example

To test for suitability as a wash-resistant, hydrophilic softener, white cotton jersey was subjected to the treatment described below with a formulation based upon the quaternary ammonium salt from Example 11. For purposes of comparison, a commercially available hydrophilic softener was used. First, the following base formulations were established:

| Invention Example 11 | Commercially available, hydrophilic softener Magnasoft ® HSSD (Osi Specialities) |
| --- | --- |
| 17.7 quaternary compound Example 11 | 20.0 g Siloxane softener |
| 0.4 g acetic acid | 0.2 g acetic acid |
| 0.3 g Na acetate | 79.8 g distilled water |
| 10.5 g Renex 36 ® (Henkel) | |
| 1.8 g Renex 30 ® (Henkel) | |
| 67.3 g distilled water | |

20 g of these base formulations were dissolved in 980 g distilled water. Then, with these formulations that effectively contain 0.35% or 0.4% siloxane agent, pieces of cotton jersey measuring 60 cm×90 cm and weighing 87 g were treated using the Foulard process. The cotton material is dipped completely in the given formulation for 5 seconds, and following the single application, the pieces are dried at 120° C. for 3 minutes.

The pieces of cloth are then separated, with one half being subjected to five machine washing cycles in the presence of a light-duty detergent (1.7 g detergent/liter of wash water). Each wash cycle lasts 25 minutes, the wash temperature is 40° C.

The hydrophilism (ability to absorb a drop of water in seconds) of the unwashed and washed textile pieces was determined, after which 5 test subjects evaluate the feel of the cloth to the touch.

| | Hydrophilism(s) | Feel |
| --- | --- | --- |
| Treated with Invention Example 11; Unwashed | 1 | Smooth, flat, soft |
| Treated with Invention Example 11; washed 5 times | <1 | Smooth, flat, medium soft |
| Commercially available hydrophilic softener; unwashed | 1 | Smooth, flat |
| Commercially available hydrophilic softener; washed 5 times | 1 | Rough |

The results show that the textile treated as specified in the invention retains the desired property combination of hydrophilism, expressed by a very short drop absorption time, and the feel to the touch that is typical of silicone.

Example 13

Fifth Embodiment of the Invention

To test for softening properties as an internal softener during the washing process, bleached strips of cotton, the surface of which was not treated in any other way, were subjected to a washing process in the presence of Ariel Futur®, Dash 2 in 1® containing bentonite, and the silicone quaternary compound described in Example 11. The following boundary conditions were maintained.

|  | Strip 1 | Strip 2 | Strip 3 |
|---|---|---|---|
| Weight of strip (g) | 12.82 | 13.06 | 13.30 |
| Quantity of water (ml) | 639 | 654 | 671 |
| Detergent | 0.63 g Ariel Futur ® | 0.66 g Ariel Futur ® | 0.67 g Dash 2 in 1 ® |
| Quaternary compound Example 11 | 0.2 g | — | — |
| Rating Ø | 1.4 | 2.8 | 1.8 |

The water is heated to 60° C., the detergents, and in the case of cotton strip 1 the silicone quaternary compound from Example 1, are dissolved in the water. The cotton strips are then washed in these solutions for 30 minutes. Afterward, the strips are rinsed in 5×600 ml water, and dried for 30 minutes at 120° C.

16 test subjects evaluated the three cotton strips for softness to the touch, and assigned each a rating, with 1 indicating the softest strip and 3 indicating the roughest strip.

The results of the evaluation gave cotton strip 1 an average rating of 1.4. The cotton strip 2 was given an average rating of 2.8, and the strip 3, which was treated with bentonite, received an average rating of 1.8.

The polysiloxane compounds specified in the invention exhibit excellent wash-resistance and substantivity.

In EP-A-282720, for example, the use of polyquaternary polysiloxanes in cosmetic formulations, especially for hair care, is described, and improved combability, a good shine, high antistatic effectiveness, and improved rinsability are generally named as the advantages.

The last mentioned characteristic, however, cannot be equated with wash resistance. While the rinsability of hair is based upon a brief onslaught main of water and very mild surfactants that will not irritate the skin, wash-resistant, hydrophilic softeners for textiles must withstand the effects of concentrated surfactant solutions having high fat and dirt dissolving power. In modern detergents, highly alkaline complexing agents, oxidative bleaching agents, and complex enzyme systems are added to these surfactant systems. The exposure frequently takes place over a period of hours at increased temperatures. For these reasons, a transfer of observations from the field of cosmetics to the field of wash-resistant fabric softeners is not possible. DE-OS 3236466, cited in the state of the art, points out that to create a wash-resistant fabric treatment, the orientation should be toward cross-linkable systems.

Similarly, it was not expected that the compounds specified in the invention would be effective as softeners in formulations for washing fibers and textiles based upon non-ionic or anionic/non-ionic surfactants. In these cases as well, the effect of the aggressive detergent formulations takes place over long periods of time at increased temperatures. This is aggravated by the fact that the original modification of the fiber surface with softening substances is eliminated.

The invention claimed is:

1. Polysiloxane compound containing:
a) At least one polyalkylene oxide structural unit with the formula:

—A—E—, —E—A—, —A—E—A', and/or —A'—E—A— wherein

A=—$CH_2C(O)O$—, —$CH_2CH_2C(O)O$—, —$CH_2CH_2CH_2C(O)O$—, —$OC(O)CH_2$—, —$OC(O)CH_2CH_2$— and/or —$OC(O)CH_2CH_2CH_2$—

A'=—$CH_2C(O)$—, —$CH_2CH_2C(O)$—, $CH_2CH_2CH_2C(O)$—, —$C(O)CH_2$—, —$C(O)CH_2CH_2$— and/or —$C(O)CH_2CH_2CH_2$—

E=a polyalkylene oxide group of the formulae:

—$[CH_2CH_2O]_q$—$[CH_2CH(CH_3)O]_r$—and/or

—$[OCH(CH_3)CH_2]_r$—$[OCH_2CH_2]_q$—

With q=1 to 200, r=0 to 200, whereby the terminal position oxygen atom of Group A binds to the terminal position —$CH_2$-group of Group E, and the terminal position carbonyl carbon atom of Group A' binds to the terminal position oxygen atom of Group E forming ester groups in each case, and/or at least one terminal position polyalkylene oxide structural unit of the formula

—A—E—$R^2$ wherein A and E have the aforementioned meaning, and $R^2$=is H, straight chain, cyclical or branched $C_1$–$C_{20}$-hydrocarbon radical, which can be interrupted by —O—, or —C(O)— and substituted with —OH, and can be acetylenic, olefinic or aromatic b) at least one bivalent or trivalent organic radical which contains at least one ammonium group, the free valences of which are saturated by structural units selected from the group consisting of structural unit a) and structural unit c), c) at least one polysiloxane structural unit with the formula:

—K—S—K—, with

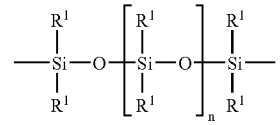

wherein $R^1$=$C_1$–$C_{22}$-alkyl, $C_1$–$C_{22}$-fluoralkyl or aryl, n=0 to 1000, end these can be identical or different if several S Groups are present in the polysiloxane compound, K=a bivalent or trivalent straight chain, cyclical or branched $C_2$–$C_{40}$ hydrocarbon residue which is optionally interrupted by —O—, —NH—,

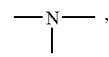

—$NR^1$—, —C(O)—, —C(S)—,

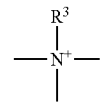

or

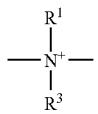

and optionally substituted with —OH, wherein
R¹ is defined as above, or represents a bond to a bivalent radical R³
R³ represents a monovalent or bivalent straight chain, cyclical or branched $C_1$–$C_{20}$ hydrocarbon radical which is optionally interrupted by —O—, —NH—, —C(O)—, —C(S)— and can be substituted with —OH, or —A—E—R², wherein A, E and R² are defined as above,
whereby the residues K can be identical or different from each other, and in the event that K represents a trivalent organic radical which contains at least one ammonium group, the saturation of the third valence takes place through a bonding to the above mentioned organic radical which contains at least one ammonium group,
d) at least one organic or inorganic acid residue for neutralization of the charges resulting from the ammonium group(s).

2. Polysiloxane compounds according to claim 1, wherein K=a bivalent or trivalent straight chain, cyclical or branched $C_2$–$C_{40}$ hydrocarbon residue which is optionally interrupted by —O—, —NH—,

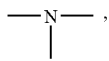

NR¹—, —C(O)—, —C(S)— and is optionally substituted with —OH, wherein R¹ is defined as above and whereby the radicals K can be identical or different from one another.

3. Polysiloxane compounds according to claim 1 or 2, wherein the previously mentioned organic radical, which contains at least one ammonium group, is a radical of the formula as component b)

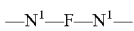
wherein
N¹ is a quaternary ammonium group of the general formula

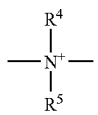

wherein
R⁴ represents a monovalent or bivalent straight chain, cyclical or branched $C_1$–$C_{20}$ hydrocarbon residue, which is interrupted by —O—, —NH—, —C(O)—, —C(S)— and optionally substituted with —OH,
R⁵ represents a monovalent straight chain, cyclical or branched $C_1$–$C_{20}$ hydrocarbon residue which can be interrupted by —O—, —NH—, —C(O)—, —C(S)— and optionally substituted with —OH, or a single bond to a bivalent radical R⁴ or a quadrivalent radical F, and the radicals R⁴ and R⁵ within the group —N¹F—N¹— as well as in the polysiloxane compound can be identical or different 1 mm one another, F=represents a bivalent or quadrivalent straight chain, cyclical or branched $C_2$–$C_{30}$ hydrocarbon radical which can be interrupted by —O—, —NH—,

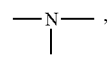

—C(O)—, —C(S) or a siloxane chain S and optionally substituted with —OH, a radical of the formula:

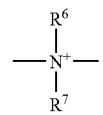

wherein R⁶=a monovalent or bivalent straight chain, cyclical or branched $C_1$–$C_{30}$ hydrocarbon radical, which is optionally interrupted by —O—, —NH—, —C(O)—, —C(S)— and optionally substituted with —OH, or optionally represents a trivalent radical K, R⁷ a monovalent straight chain, cyclical or branched $C_1$–$C_{20}$ hydrocarbon radical which is optionally interrupted by —O—, —NH—, —C(O)—, —C(S)— and is optionally substituted with —OH, or —A—E—R²; wherein —A—E—R² has the aforementioned meaning, or represents a single bond to a bivalent radical R⁶ or to a trivalent radical K and the radicals R⁶ and R⁷ can be identical or different from each other, or is a radical of the formula

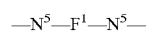

wherein
N⁵ is an ammonium group of the general formula

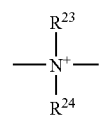

wherein
R²³ represents hydrogen, a monovalent or bivalent straight chain, cyclical or branched $C_1$–$C_{20}$ hydrocarbon radical which is optionally interrupted by —O—, —NH—, —C(O)—, —C(S)— and optionally substituted with —OH, R²⁴ represents hydrogen, a monovalent straight chain, cyclical or branched $C_1$–$C20$ hydrocarbon radical which is optionally interrupted by —O—, —NH—, —C(O)—, —C(S)— and optionally substituted with —OH, or represents a single bond to a bivalent radical R²³, and the radicals R²³ and R²⁴ can be identical or different from each other inside the group —N⁵—F¹—N⁵— as well as in the polysiloxane compound, F¹=represents a bivalent straight chain, cyclical or branched hydrocarbon radical which is optionally interrupted by —O—, —NH—,

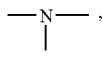

—C(O)—, —C(S)— or by the group —E—, and wherein in the event that more than one group $N^5$ or $F^1$ is present, a majority of said $N^5$ groups can be identical or different from one another and a majority of said $F^1$ groups can be identical or different from one another.

4. Polysiloxanes according to claim 3 of the formula (I), $$—[B—N^1—F—N^1]_m— \quad (I)$$

wherein m=2 to 500,

B is selected from the group consisting of —A—E—K—S—K—E—A—, —A—E—A'— and —A'—E—A—, with the proviso that at least one group B is —A—E—K—S—K—E—A—, and the proportion of Group —A—E—A'— or —A'—E—A— in Group B, if present, is selected to result in the mass of —A—E—A'— or —A'—E—A— being 0 to 90% of the mass of the polysiloxane component S in the polymer.

5. Polysiloxane compound according to claim 1 or 2 of the formula (II), $$R^2—E—A—N^2—K—S—K—N^2—A—E—R^2 \quad (II)$$

wherein S, K, —A—E—, —E—A— and $R^2$ have the aforementioned meanings and $N^2$ is an organic radical which contains at least one quaternary ammonium group of the general formula

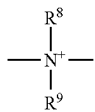

wherein $R^8$=a monovalent or bivalent straight chain, cyclical or branched $C_1$–$C_{20}$ hydrocarbon radical which is optionally interrupted by —O—, —NH—, —C(O)—, —C(S)— and optionally substituted by —OH, $R^9$ a monovalent straight chain, cyclical or branched $C_1$–$C_{20}$ hydrocarbon radical which is optionally interrupted by —O—, —NH—, —C(O)—, —C(S)— and optionally substituted with —OH, or represents a single bond to a bivalent radical $R^8$ or to a trivalent radical K, and the radicals $R^8$ and $R^9$ can be identical or different from each other within the polysiloxane compound of general formula (II).

6. Polysiloxane compound according to claim 1 or 2 of formula (III), $$—[K—S—K—N^3]_m— \quad (III)$$

in which

S, K and m are defined as above, $N^3$ is an organic radical which contains at least one ammonium group of the formula

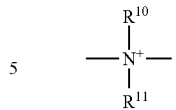

wherein $R^{10}$ a monovalent straight chain, cyclical or branched $C_1$–$C_{30}$ hydrocarbon radical which can be interrupted by —O—, —NH—, —C(O)—, —C(S)— and is optionally substituted by —OH or represents a single bond to K, $R^{11}$=—A—E—$R^2$, wherein —A—E—$R^2$ has the aforementioned meaning, and m=2–500.

7. Polysiloxane compounds according to claim 1 or 2 of formula (IV), $$—[N^4—K—S—K—N^4—A—E—A']_m— \text{ or } —[N^4—K—S—K—N^4—A'—E—A]_m— \quad (IV)$$

wherein m=2–500, and $N^4$ is an organic radical which contains at least one quaternary ammonium group of the general formula

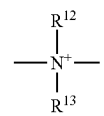

wherein $R^{12}$ is a monovalent or bivalent straight chain, cyclical or branched $C_1$–$C_{20}$ hydrocarbon radical which is optionally interrupted by —O—, —NH—, —C(O)—, —C(S)— and optionally substituted with —OH, $R^{13}$ can have the meanings of $R^{12}$ or represents a single bond to K or $R^{12}$, and the radicals $R^{12}$ and $R^{13}$ can be identical or different from each other.

8. Polysiloxane compound according to claim 1 or 2 of general formula (V)

$$—[N^5—F^1—N^5—Y—]_m \quad (V)$$

wherein

Y is a group of the formula

—K—S—K— and optionally in addition also includes a proportion of a group of the formula

—A—E—A'— or —A'—E—A—, wherein m=2–500, the groups K, 8, —A—E—A'— and —A'—E—A— can be identical or different from each other within the polysiloxane compounds of general formula (V), and the molar ratio of Group —K—S—K— and Group —A—E—A'— or —A'—E—A— in the polysiloxane compound of general formula (V) is from 100:1 to 1:100, $N^5$ is an ammonium group of the general formula

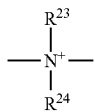

wherein
$R^{23}$ represents hydrogen, a monovalent or bivalent straight chain, cyclical or branched $C_1$–$C_{20}$ hydrocarbon radical which is optionally interrupted by —O—, —NH—, —C(O)—, —C(S)— and optionally substituted by —OH, $R^{24}$ represents hydrogen, a monovalent straight chain, cyclical or branched $C_1$–$C_{20}$ hydrocarbon radical which is optionally interrupted by —O—, —NH—, —C(O)—, —C(S)— and optionally substituted with —OH, or represents a single bond to a bivalent radical $R^{23}$, and the radicals $R^{23}$ and $R^{24}$ can be identical or different from each other within the Group —$N^5$—$F^1$—$N^5$— as well as in the polysiloxane compound $F^1$=represents a bivalent straight chain, cyclical or branched hydrocarbon residue which is optionally interrupted by —O—, —NH—, trivalent N, —C(O)—, —C(S)— or by a Group E, wherein E is defined as above, and wherein, in the event that more than one $N^5$ or $F^1$ group is present, the majority of said groups can be identical or different from each other.

9. A composition of claim 1, wherein said composition is a cosmetic formulation for skin and hair care, a polish for the treatment and outfitting of hard surfaces, a formulation for drying automobiles and other hard surfaces, for initial outfitting of textiles and textile fibers, a softener for application after washing textiles with non-ionogenic or anionic/non-ionogenic detergent formulations, softener in formulations for textile washes based upon non-ionic or anionic/non-ionic surfactants or an agent for preventing or reversing textile crumpling.

10. A method for softening textiles after washing with non-ionogenic or anionic/non-ionogenic detergent formulations which comprises applying the polysiloxane of claim 1 or 2 to said textiles.

* * * * *